US008658825B2

(12) United States Patent
Abdur-Rashid et al.

(10) Patent No.: US 8,658,825 B2
(45) Date of Patent: Feb. 25, 2014

(54) METHOD FOR THE PREPARATION OF AMINOPHOSPHINE LIGANDS AND THEIR USE IN METAL CATALYSTS

(75) Inventors: Kamaluddin Abdur-Rashid, Mississauga (CA); Rongwei Guo, Mississauga (CA); Xuanhua Chen, Mississauga (CA); Wenli Jia, Mississauga (CA)

(73) Assignee: Kanata Chemical Technologies Inc., Toronto, Ontario (CA)

( * ) Notice: Subject to any disclaimer, the term of this patent is extended or adjusted under 35 U.S.C. 154(b) by 822 days.

(21) Appl. No.: 12/663,369

(22) PCT Filed: Jun. 9, 2008

(86) PCT No.: PCT/CA2008/001076
§ 371 (c)(1),
(2), (4) Date: Apr. 15, 2010

(87) PCT Pub. No.: WO2008/148202
PCT Pub. Date: Dec. 11, 2008

(65) Prior Publication Data
US 2010/0204514 A1 Aug. 12, 2010

Related U.S. Application Data

(60) Provisional application No. 60/942,699, filed on Jun. 8, 2007.

(30) Foreign Application Priority Data

Jun. 8, 2007 (CA) .................................. 2591126

(51) Int. Cl.
*C07F 9/02* (2006.01)
(52) U.S. Cl.
USPC .............................................. 564/15; 564/12
(58) Field of Classification Search
USPC ....................................................... 564/15, 12
See application file for complete search history.

(56) References Cited

U.S. PATENT DOCUMENTS 6,590,115 B2 7/2003 Boaz et al.

FOREIGN PATENT DOCUMENTS

WO WO 02/22526 3/2002

OTHER PUBLICATIONS

Improved and Efficient Synthesis of Chiral N,P-Ligands via Cyclic Sulfamidates for Asymmetric Addition of Butyllithium to Benzaldehyde. Ronnholm, P et al. Org. Lett. Aug. 16, 2007, 9(19), 3781-3783.*
Issleib K and Oehne H., Chem. Ber. 1967, 100, 2685-2693.*
Bunlaksananusorn T, "Novel Synthesis of Chiral 1,2-Aminophosphine Ligands and Their Applications in Asymmetric Catalysis" PhD Thesis, Univ Munich, 2003, p. 12.*
Abdur-Rashid. K; Lough, A.J.; Morris, R.H. Organometallics 2000, 19, 2655-2657.
Abdur-Rashid, K.; Lough, A.J.; Morris, R.H. Organometallics 2001, 20, 1047-1049.
Abdur-Rashid, K.; Guo, R.; Lough, A.J.; Morris, R.H. Adv. Synth. Catal. 2005, 347, 571-579.
Doucet, H.; Ohkuma, T.; Murata, K.; Yokozawa, T.; Kozawa, M.; Katayama, E.; England, A.F.; Ikariya, T.; Noyori, R. Angew. Chem., Int. Ed. 1998, 37, 1703-1707.
Guo, R.; Lough, A.J.; Morris, R.H.; Song, D. Organometallics 2004, 23, 5524-5529.
Guo, R.; Lough, A.J.; Morris, A.J.; Song, D. Organometallics 2005, 24 3354-3354.
Issleib, K et al. "Syntheses und Reaktionsverhalten des Iβ-amino-äthyl)-phenyl-phosphins". Chern. Bel'. 1967,100,2685-2693.
Jiang, Q et al. "Synthesis of(IR, IR')-2,6-Bis(1-(diphenylphosphio)ethYlJpyridine and its Application in Asyimnetrc Transfer Hydrogenation" Tetrahedron Letters 1996, 37(6), 79.
Külmlein, C. "Ruthenium (II) Complexes bearing Bis(phosphine) and β-Aininophosphine Ligands and their Application to Homogenous ;:C=O Reduction". Doctoral thesis. 2005.
Mikami, K.; Korenaga, T.; Terada, M.; Ohkuma, T.; Pham, T.; Noyori, R. Angew. Chem., Int. Ed.. 1999, 38, 495-497.
Ohkuma, T.; Ooka, H.; Ikariya, T.; Noyori, R. J. Am. Chem. Soc. 1995, 117, 10417-10418.
Ohkuma, T.; Koizumi, M.; Doucet, H.; Pham, T.; Kozawa, M.; Murata, K.; Katayama, E.; Yokozawa, T.; Ikariya, T.; Noyori, R. J. Am. Chem. Soc. 1998, 120, 13529-13530.
Ohkuma, T.; Doucet, H.; Pham, T.; Mikami, K.; Korenaga, T.; Terada, M.; Noyori, R. J. Am. Chem. Soc. 1998, 120, 1086-1087.
Romùioltn, P et al. "Improved ooid Effcient Synthesis of Chiral N,P-Ligands via Cyclic Sulfamidates for Asymmetric Addition of Butyllithimn to Benzaldehyde". Org. Lett. Aug. 2007 (9), 3781-3.
Andrieu, Jacques. et al. "Synthesis Coordination to Rh(I), and Hydroformylation Catalysis of New [beta]-Aminophosphines Bearing a Dangling Nitrogen Group: An Unusual Inversion of a Rh-Coordinated P Center". Inorganic Chemistry. 41(15):3876-3885, 2002.

(Continued)

*Primary Examiner* — Johann R Richter
*Assistant Examiner* — Kofi Adzamli
(74) *Attorney, Agent, or Firm* — Bereskin & Parr LLP/S.E.N.C.R.L., s.r.l.; Michael Fenwick

(57) ABSTRACT

The present application is directed to i) a method for synthesizing aminophosphine (P,N) and phosphine-aminophosphine (P,N,P) ligands, ii) the use of such ligands in the preparation of metal complexes as hydrogenation catalysts, and iii) aminophosphine (P,N) and phosphine-aminophosphine (P,N,P) ligands of various structures. In particular, the methods in i) involve reacting a protected tertiary amine of formula (I) with a metal phosphide of the formula Y—PR8R9 to afford an aminophosphine of formula (II), which can then be optionally further reacted with a phosphine of the formula (III) to afford the phosphine-aminophosphine of formula (IV).

8 Claims, 3 Drawing Sheets

(56) References Cited

OTHER PUBLICATIONS

Krawiecka, B. et al. "Stereocontrolled Synthesis of 3-Amino-2-Hydroxyalkyl Diphenylphophine Oxides Mediated by Chiral Azetidinium Salts and Epoxyamines", Tetrahedron Letters, Elsevier, Amsterdam, NL. 46(25):4381-4384, 2005.

Mikhael et al., "A P,N Ligand with Central and Axial Chiral Elements: Synthesis and Application in a Allylic Alkylation". Tetrahedron Asymmetry, Pergamon Press Ltd. Oxford, GB. 17(12):1853-1858, 2006.

Soeta, Takahiro et al. "Asymmetric Alkylation of N-Toluenesufonylimines with Dialkylzinc Reagents Catalyzed by Copper-Chiral Amidophosphine". The Journal of Organic Chemistry. 68(25):9723-9727, 2003.

* cited by examiner

METHOD FOR THE PREPARATION OF AMINOPHOSPHINE LIGANDS AND THEIR USE IN METAL CATALYSTS

CROSS REFERENCE TO RELATED APPLICATIONS

This is a national stage application of PCT/CA2008/001076 filed on Jun. 9, 2008 which claims priority from U.S. provisional application 60/942,699 filed on Jun. 8, 2007 and Canadian Application No. 2,591,126 filed on Jun. 8, 2007, which are incorporated herein by reference in their entirety.

FIELD OF THE DISCLOSURE

The present disclosure relates to a general procedure for the synthesis of a wide range of achiral and chiral aminophosphine ligands, and their use for the preparation of chiral and achiral metal aminophosphine catalysts, for example, for the hydrogenation of ketones, aldehydes and imines.

BACKGROUND OF THE DISCLOSURE

Catalytic hydrogenation is a fundamental reaction in chemistry, and is used in a large number of chemical processes. Catalytic hydrogenation of ketones and aldehydes are useful and indispensable processes for the synthesis of alcohols, which are valuable end products and precursor chemicals in the pharmaceutical, agrochemical, flavor, fragrance, material and fine chemical industries.[1]

To achieve a catalytic hydrogenation transformation in the reduction of ketones and aldehydes, molecular hydrogen ($H_2$) is used. However, for the hydrogenation process to proceed, a catalyst or catalytic system is needed to activate the molecular hydrogen.

Noyori and co-workers developed the versatile $RuCl_2(PR_3)_2$(diamine) and $RuCl_2$(diphosphine)(diamine) hydrogenation catalyst system that are highly effective for the hydrogenation of ketones.[2] It was subsequently discovered that the Noyori catalysts were effective for the reductive hydrogenation of imines to amines.[3]

It was also determined that ruthenium aminophosphine complexes of the type $RuCl_2$(aminophosphine)$_2$ and $RuCl_2$(diphosphine)(aminophosphine) are also very effective catalysts for the hydrogenation of ketones, aldehydes and imines, including the preparation of chiral compounds.[4] Hence, these catalysts are versatile alternatives to the Noyori-type catalysts.

Currently, the availability of chiral and achiral aminophosphine ligands are severely limited which restricts the development and exploitation of $RuCl_2$(aminophosphine)$_2$ and $RuCl_2$(diphosphine)(aminophosphine) catalysts in catalytic hydrogenation processes. The few reported syntheses of aminophosphine ligands are either low yielding or involve the use of aziridines.[5]

Hence, there remains a need for a facile synthesis of chiral and achiral aminophosphine ligands in high yields and purity, and suitable for large scale applications.

SUMMARY OF THE DISCLOSURE

It has now been found that achiral and chiral aminophosphine ligands can be synthesized in high yield and with high purity, allowing access to a wide variety of ligands from readily available and inexpensive starting materials.

Accordingly, the present disclosure includes a method for preparing aminophosphine ligands comprising reacting a compound of the formula I

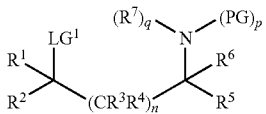

with a metal phosphide reagent of the formula $Y\text{—}PR^8R^9$ under conditions to provide, after removal of PG, a compound of the formula II,

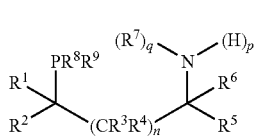

wherein
$LG^1$ is a suitable leaving group;
q is 0 or 1;
p is 1 or 2, where when p is 1, the N atom is further linked to $R^7$ or any one of $R^1$, $R^2$, $R^3$, $R^4$, $R^5$, $R^6$ or LG, and when N is linked to any one of $R^1$, $R^2$, $R^3$, $R^4$, $R^5$, $R^6$ or LG, or if p is 2, q is 0;
n is 0, 1, 2, 3 or 4;
PG is a suitable amine protecting group and, when p is 2, PG is the same or different;
Y is a cation;
$R^1$ to $R^6$ are simultaneously or independently selected from H, $C_{1-20}$alkyl, $C_{2-20}$alkenyl, $C_{2-20}$alkynyl, $C_{3-20}$cycloalkyl, aryl and heteroaryl, said latter 6 groups being optionally substituted, or two adjacent or geminal groups, including the nitrogen atom of the amino group, are linked together to form an optionally substituted monocyclic or polycyclic, metalated, saturated, unsaturated and/or aromatic ring system having 3 or more atoms;
$R^7$ is selected from $C_{1-6}$alkyl and aryl, said latter two groups being optionally substituted;
$R^8$ and $R^9$ are simultaneously or independently selected from H, $C_{1-20}$alkyl, $C_{2-20}$alkenyl, $C_{2-20}$alkynyl, aryl, heteroaryl, $OR^{10}$ and $N(R^{10})_2$, said latter 7 groups being optionally substituted, or $R^8$ and $R^9$ are linked together to form an optionally substituted monocyclic or polycylic, saturated, unsaturated and/or aromatic ring system having 4 or more atoms, including the phosphorous atom to which said $R^8$ and $R^9$ groups are linked, and in which one or more carbon atoms in said monocyclic or polycyclic ring system are optionally replaced with a heteromoiety selected from O, S, N, NH and $NC_{1-6}$alkyl;
$R^{10}$ is selected from $C_{1-6}$alkyl, $C_{2-6}$alkenyl, $C_{2-6}$alkynyl and aryl, said latter 4 groups being optionally fluoro-substituted;
the optional substituents are selected from one or more of halo, OH, $NH_2$, $OR^{11}$, $N(R^{11})_2$ and $R^{11}$; and
$R^{11}$ is selected from $C_{1-6}$alkyl, $C_{2-6}$alkenyl, $C_{2-6}$alkynyl and aryl, said latter 4 groups being optionally fluoro-substituted.

In another aspect, the present disclosure includes a method for preparing aminophosphine ligands comprising reacting a compound of the formula II

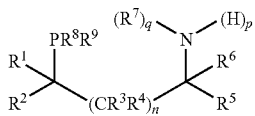

with a compound of the formula III

under conditions to provide a compound of the formula IV

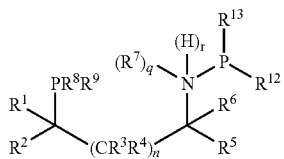

wherein
$LG^2$ is a suitable leaving group;
one of q and r is 1, while the other is 0;
n is 0, 1, 2, 3 or 4;
$R^1$ to $R^6$ are simultaneously or independently selected from H, $C_{1-20}$alkyl, $C_{2-20}$alkenyl, $C_{2-20}$alkynyl, $C_{3-20}$cycloalkyl, aryl and heteroaryl, said latter 6 groups being optionally substituted, or two adjacent or geminal groups, including the nitrogen atom of the amino group, are linked together to form an optionally substituted monocyclic or polycyclic, metalated, saturated, unsaturated and/or aromatic ring system having 3 or more atoms;
$R^7$ is selected from $C_{1-6}$alkyl and aryl, said latter two groups being optionally substituted;
$R^8$ and $R^9$ are simultaneously or independently selected from H, $C_{1-20}$alkyl, $C_{2-20}$alkenyl, $C_{2-20}$alkynyl, aryl, heteroaryl, $OR^{10}$ and $N(R^{10})_2$, said latter 7 groups being optionally substituted, or $R^8$ and $R^9$ are linked together to form an optionally substituted monocyclic or polycyclic, saturated, unsaturated and/or aromatic ring system having 4 or more atoms, including the phosphorous atom to which said $R^8$ and $R^9$ groups are linked, and in which one or more carbon atoms in said monocyclic or polycyclic ring system are optionally replaced with a heteromoiety selected from O, S, N, NH and $NC_{1-6}$alkyl;
$R^{10}$ is selected from $C_{1-6}$alkyl, $C_{2-6}$alkenyl, $C_{2-6}$alkynyl and aryl, said latter 4 groups being optionally fluoro-substituted; the optional substituents are selected from one or more of halo, OH, $NH_2$, $OR^{11}$, $N(R^{11})_2$ and $R^{11}$; and
$R^{11}$ is selected from $C_{1-6}$alkyl, $C_{2-6}$alkenyl, $C_{2-6}$alkynyl and aryl, said latter 4 groups being optionally fluoro-substituted; and
$R^{12}$ and $R^{13}$ are simultaneously or independently selected from H, $C_{1-20}$alkyl, $C_{2-20}$alkenyl, $C_{2-20}$alkynyl, aryl, heteroaryl, $OR^{10}$ and $N(R^{10})_2$, said latter 7 groups being optionally substituted, or $R^{12}$ and $R^{13}$ are linked together to form an optionally substituted monocyclic or polycyclic, saturated, unsaturated and/or aromatic ring system having 4 or more atoms, including the phosphorous atom to which said $R^{12}$ and $R^{13}$ groups are linked, and in which one or more carbon atoms in said monocyclic or polycyclic ring system are optionally replaced with a heteromoiety selected from O, S, N, NH and $NC_{1-6}$alkyl.

In another aspect of the disclosure, the aminophosphine ligands are complexed with a metal to form aminophosphine metal catalysts.

In another aspect of the disclosure, the aminophosphine metal catalysts are useful for the hydrogenation of ketones, aldehydes and imines.

In another aspect of the disclosure, there is included novel aminophosphepine ligands of the formula V

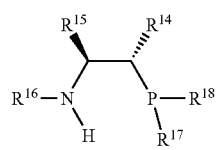

wherein
$R^{14}$ and $R^{15}$ are simultaneously or independently selected from H, $C_{1-20}$alkyl, $C_{2-20}$alkenyl, $C_{2-20}$alkynyl, $C_{3-20}$cycloalkyl, aryl and heteroaryl, said latter 6 groups being optionally substituted;
$R^{16}$ is selected from H, $C_{1-6}$alkyl and aryl, said latter two groups being optionally substituted or $R^{16}$ is $PR^{19}R^{20}$;
or two of $R^{14}$, $R^{15}$ and $R^{16}$ are linked to form an optionally substituted monocyclic or polycyclic, metalated, saturated, unsaturated and/or aromatic ring system having 3 or more atoms;
$R^{17}$ and $R^{18}$ are linked together with the phosphorous atom to which said $R^{17}$ and $R^{18}$ groups are linked to form an optionally substituted polycyclic ring of the formula

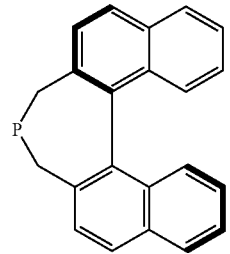

in which one or more carbon atoms in said polycyclic ring system are optionally replaced with a heteromoiety selected from O, S, N, NH and $NC_{1-6}$alkyl;
$R^{19}$ and $R^{20}$ are simultaneously or independently selected from H, $C_{1-20}$alkyl, $C_{2-20}$alkenyl, $C_{2-20}$alkynyl, aryl, heteroaryl, $OR^{21}$ and $N(R^{21})_2$, said latter 7 groups being optionally substituted, or $R^{19}$ and $R^{20}$ are linked together to form an optionally substituted monocyclic or polycyclic, saturated, unsaturated and/or aromatic ring system having 4 or more atoms, including the phosphorous atom to which said $R^{19}$ and $R^{20}$ groups are linked, and in which one or more carbon atoms in said monocyclic or polycyclic ring system are optionally replaced with a heteromoiety selected from O, S, N, NH and $NC_{1-6}$alkyl;
the optional substituents are selected from one or more of halo, OH, $NH_2$, $OR^{22}$, $N(R^{22})_2$ and $R^{22}$; and
$R^{21}$ and $R^{22}$ are independently selected from $C_{1-6}$alkyl, $C_{2-6}$alkenyl, $C_{2-6}$alkynyl and aryl, said latter 4 groups being optionally fluoro-substituted.

In an embodiment of the disclosure, there is included a novel aminophosphine ligand of the Formulae VI or VII

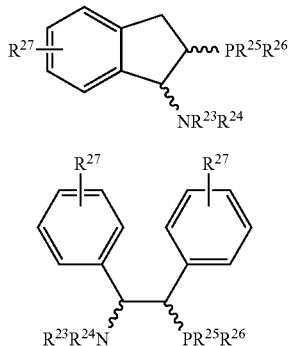

wherein $R^{23}$ and $R^{24}$ are simultaneously or independently selected from H, $C_{1-6}$alkyl and aryl, said latter two groups being optionally substituted or one of $R^{23}$ and $R^{24}$ is $PR^{28}R^{29}$;

$R^{25}$ and $R^{26}$ are simultaneously or independently selected from H, $C_{1-20}$alkyl, $C_{2-20}$alkenyl, $C_{2-20}$alkynyl, aryl, heteroaryl, $OR^{30}$ and $N(R^{30})_2$, said latter 7 groups being optionally substituted, or $R^{25}$ and $R^{26}$ are linked together to form an optionally substituted monocyclic or polycylic, saturated, unsaturated and/or aromatic ring system having 4 or more atoms, including the phosphorous atom to which said $R^{25}$ and $R^{26}$ groups are linked, and in which one or more carbon atoms in said monocyclic or polycyclic ring system are optionally replaced with a heteromoiety selected from O, S, N, NH and $NC_{1-6}$alkyl;

$R^{27}$ represents optional substituents selected from one or more of OH, $NH_2$, $OR^{31}$, $N(R^{31})_2$ and $R^{31}$, alternatively, $R^{27}$ is H;

$R^{28}$ and $R^{29}$ are simultaneously or independently selected from H, $C_{1-20}$alkyl, $C_{2-20}$alkenyl, $C_{2-20}$alkynyl, aryl, heteroaryl, $OR^{32}$ and $N(R^{32})_2$, said latter 7 groups being optionally substituted, or $R^{28}$ and $R^{29}$ are linked together to form an optionally substituted monocyclic or polycyclic, saturated, unsaturated and/or aromatic ring system having 4 or more atoms, including the phosphorous atom to which said $R^{28}$ and $R^{29}$ groups are linked, and in which one or more carbon atoms in said monocyclic or polycyclic ring system are optionally replaced with a heteromoiety selected from O, S, N, NH and $NC_{1-6}$alkyl;

$R^{30}$, $R^{31}$ and $R^{32}$ are independently selected from $C_{1-6}$alkyl, $C_{2-6}$alkenyl, $C_{2-6}$alkynyl and aryl, said latter 4 groups being optionally fluoro-substituted;

the optional substituents are selected from one or more of halo, OH, $NH_2$, $OR^{33}$, $N(R^{33})_2$ and $R^{33}$; and $R^{33}$ is selected from $C_{1-6}$alkyl, $C_{2-6}$alkenyl, $C_{2-6}$alkynyl and aryl, said latter 4 groups being optionally fluoro-substituted.

Also included within the disclosure are metal complexes, suitably a transition metal complex comprising a ligand of the formula II, IV, V, VI or VII.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

The disclosure will now be described in greater detail with reference to the following drawings in which.

DETAILED DESCRIPTION OF THE DISCLOSURE

Definitions

Figure 1:
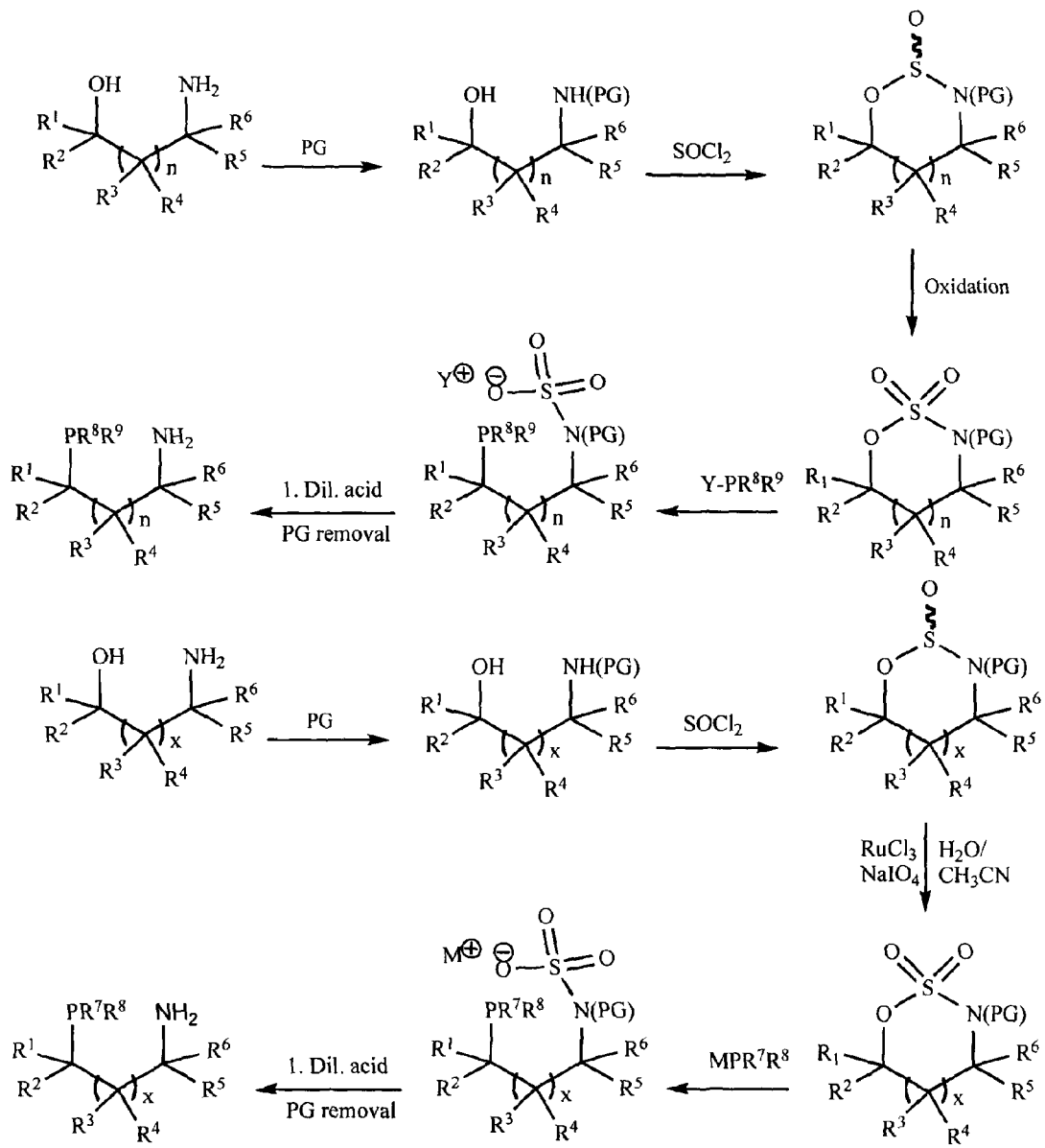
FIG. 1 is a schematic showing the method of producing an aminophosphine ligand in accordance with one embodiment of the disclosure.

The term "$C_{1-n}$alkyl" as used herein means straight and/or branched chain, saturated alkyl groups containing from one to "n" carbon atoms and includes (depending on the identity of n) methyl, ethyl, propyl, isopropyl, n-butyl, s-butyl, isobutyl, t-butyl, 2,2-dimethylbutyl, n-pentyl, 2-methylpentyl, 3-methylpentyl, 4-methylpentyl, n-hexyl and the like, where the variable n is an integer representing the largest number of carbon atoms in the alkyl radical.

The term "$C_{2-n}$alkenyl" as used herein means straight and/or branched chain, unsaturated alkyl groups containing from one to n carbon atoms and one to three double bonds, and includes (depending on the identity of n) vinyl, allyl, 2-methylprop-1-enyl, but-1-enyl, but-2-enyl, but-3-enyl, 2-methylbut-1-enyl, 2-methylpent-1-enyl, 4-methylpent-1-enyl, 4-methylpent-2-enyl, 2-methylpent-2-enyl, 4-methylpenta-1,3-dienyl, hexen-1-yl and the like, where the variable n is an integer representing the largest number of carbon atoms in the alkenyl radical.

The term "$C_{2-n}$alkynyl" as used herein means straight and/or branched chain, unsaturated alkyl groups containing from one to n carbon atoms and one to three triple bonds, and includes (depending on the identity of n) ethynyl, 1-propynyl, 2-propynyl, 2-methylprop-1-ynyl, 1-butynyl, 2-butynyl, 3-butynyl, 1,3-butadiynyl, 3-methylbut-1-ynyl, 4-methylbutynyl, 4-methylbut-2-ynyl, 2-methylbut-1-ynyl, 1-pentynyl, 2-pentynyl, 3-pentynyl, 4-pentynyl, 1,3-pentadiynyl, 1,4-pentadiynyl, 3-methylpent-1-ynyl, 4-methylpent-2-ynyl 4-methylpent-2-ynyl, 1-hexynyl and the like, where the variable n is an integer representing the largest number of carbon atoms in the alkynyl radical.

The term "$C_{3-20}$cycloalkyl" as used herein means a monocyclic or polycyclic saturated carbocylic group containing from three to twenty carbon atoms and includes cyclopropyl, cyclobutyl, cyclopentyl, cyclodecyl and the like.

The term "aryl" as used herein means a monocyclic or polycyclic aromatic ring system containing from 6 to 14 carbon atoms and at least one aromatic group and includes phenyl, naphthyl, anthracenyl, 1,2-dihydronaphthyl, 1,2,3,4-tetrahydronaphthyl, fluorenyl, indanyl, indenyl, ferrocenyl and the like.

The term "heteroaryl" as used herein means a monocyclic or polycyclic ring system containing one or two aromatic rings and from 5 to 14 atoms of which, unless otherwise specified, one, two, three, four or five are heteromoieties independently selected from N. NH, N($C_{1-6}$alkyl), O and S and includes thienyl, furyl, pyrrolyl, pyrididyl, indolyl, quinolyl, isoquinolyl, tetrahydroquinolyl, benzofuryl, benzothienyl and the like.

The term "ring system" as used herein refers to any type of cyclic structure that comprises one or more rings and any type of saturation and optionally includes, where indicated, heteromoieties or metals. Ring systems formed between two R groups or an R group and a heteroatom, include within the system the atoms to which the R groups and/or heteroatoms are attached and any atoms linking the atoms to which the R groups and/or heteroatoms are attached.

The term "fluoro-substituted" with respect to any specified group as used herein means that the one or more, including all, of the hydrogen atoms in the group have been replaced with a fluorine, and includes trifluoromethyl, pentafluoroethyl, fluoromethyl and the like.

The term "halo" as used herein means halogen and includes chloro, fluoro, bromo and iodo.

All compounds and groups having the general formulae disclosed and described herein, unless otherwise indicated, comprise carbon atoms and where no substitution is indicated in the structural formulae, the carbon atoms comprise hydrogen atoms to fulfill the valency requirements of carbon. In certain embodiments, and where indicated, one or more, although not all, of the carbon atoms in the group are replaced with another atom.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

METHOD OF THE DISCLOSURE

It has been found that achiral and chiral aminophosphine ligands can be synthesized in high yield and with high purity, allowing access to a wide variety of ligands from readily available and inexpensive starting materials. Accordingly, a method for producing achiral and chiral aminophosphine ligands is disclosed.

In an embodiment of the disclosure, a method for preparing aminophosphine ligands comprising reacting a compound of the formula I

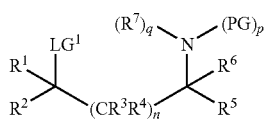

I with a metal phosphide reagent of the formula Y—$PR^8R^9$ under conditions to provide, after removal of PG, a compound of the formula II,

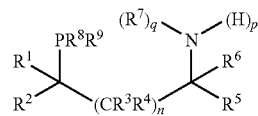

II wherein
$LG^1$ is a suitable leaving group;
q is 0 or 1;
p is 1 or 2, where when p is 1, the N atom is further linked to $R^7$ or any one of $R^1$, $R^2$, $R^3$, $R^4$, $R^5$, $R^6$ or LG, and when N is linked to any one of $R^1$, $R^2$, $R^3$, $R^4$, $R^5$, $R^6$ or LG, or if p is 2, q is 0;
n is 0, 1, 2, 3 or 4;
PG is a suitable amine protecting group and, when p is 2, PG is the same or different;
Y is a cation;
$R^1$ to $R^6$ are simultaneously or independently selected from H, $C_{1-20}$alkyl, $C_{2-20}$alkenyl, $C_{2-20}$alkynyl, $C_{3-20}$cycloalkyl, aryl and heteroaryl, said latter 6 groups being optionally substituted, or two adjacent or geminal groups, including the nitrogen atom of the amino group, are linked together to form an optionally substituted monocyclic or polycyclic, metalated, saturated, unsaturated and/or aromatic ring system having 3 or more atoms;
$R^7$ is selected from $C_{1-6}$alkyl and aryl, said latter two groups being optionally substituted;
$R^8$ and $R^9$ are simultaneously or independently selected from H, $C_{1-20}$alkyl, $C_{2-20}$alkenyl, $C_{2-20}$alkynyl, aryl, heteroaryl, $OR^{10}$ and $N(R^{10})_2$, said latter 7 groups being optionally substituted, or $R^8$ and $R^9$ are linked together to form an optionally substituted monocyclic or polycylic, saturated, unsaturated and/or aromatic ring system having 4 or more atoms, including the phosphorous atom to which said $R^8$ and $R^9$ groups are linked, and in which one or more carbon atoms in said monocyclic or polycyclic ring system are optionally replaced with a heteromoiety selected from O, S, N, NH and $NC_{1-6}$alkyl;
$R^{10}$ is selected from $C_{1-6}$alkyl, $C_{2-6}$alkenyl, $C_{2-6}$alkynyl and aryl, said latter 4 groups being optionally fluoro-substituted;
the optional substituents are selected from one or more of halo, OH, $NH_2$, $OR^{11}$, $N(R^{11})_2$ and $R^{11}$; and
$R^{11}$ is selected from $C_{1-6}$alkyl, $C_{2-6}$alkenyl, $C_{2-6}$alkynyl and aryl, said latter 4 groups being optionally fluoro-substituted.

In an embodiment of the present disclosure, $R^1$ to $R^6$ are simultaneously or independently selected from H, $C_{1-10}$alkyl, $C_{2-10}$alkenyl, $C_{2-10}$alkynyl, $C_{3-10}$cycloalkyl, aryl and heteroaryl, said latter 6 groups being optionally substituted, or two adjacent or geminal groups, including the nitrogen atom of the amino group, are linked together to form an optionally substituted monocyclic or polycyclic, metallated, saturated, unsaturated and/or aromatic ring system having 5 or more atoms. In further embodiments of the disclosure, $R^1$ to $R^6$ are simultaneously or independently selected from H, $C_{1-4}$alkyl, $C_{2-4}$alkenyl, $C_{2-4}$alkynyl, $C_{3-6}$cycloalkyl, aryl and heteroaryl, said latter 6 groups being optionally substituted, or two adjacent or geminal groups, including the carbons to which these groups are attached and/or the nitrogen atom of the nitrogen atom of the amino group, are linked together to form an optionally substituted monocyclic or polycyclic, metallated, saturated, unsaturated and/or aromatic ring system having 5 or more atoms. In further embodiments of the disclosure, $R^1$ to $R^6$ are simultaneously or independently selected from H, methyl, phenyl, or two adjacent or geminal groups and the carbons to which said groups are attached and/or the nitrogen atom of the amino group, are linked together to form phenyl, indanyl or ferrocenyl, or a pyrrolidinyl ring.

In embodiments of the present disclosure, n is equal to 0, 1 or 2. In further embodiments of the disclosure, n is 0 or 1.

In other embodiments of the present disclosure, $R^7$ is $C_{1-4}$alkyl or phenyl, said latter two groups being optionally substituted. In another embodiment, $R^7$ is methyl.

In further embodiments of the present disclosure, $R^8$ and $R^9$ are simultaneously or independently selected from H, $C_{1-10}$alkyl, $C_{2-10}$alkenyl, $C_{2-10}$alkynyl and aryl, said latter 4 groups being optionally substituted, or $R^8$ and $R^9$ are linked together to form an optionally substituted monocyclic or polycyclic ring system having 4 or more atoms, including the phosphorous atom to which $R^8$ and $R^9$ are linked, in which the rings are saturated, unsaturated and/or aromatic and in which one or more carbon atoms in said monocyclic or polycyclic ring system are optionally replaced with a heteromoiety selected from O, N, NH and $NC_{1-6}$alkyl. In further embodiments of the disclosure, $R^8$ and $R^9$ are simultaneously or independently selected from H, $C_{1-6}$alkyl, $C_{2-6}$alkenyl, $C_{2-6}$alkynyl, phenyl, and naphthyl, said latter 5 groups being optionally substituted, or $R^8$ and $R^9$ are linked to form an optionally substituted monocylic, fused bicylic, fused tricyclic, fused quadracyclic or fused pentacyclic ring system having 4-23 atoms, including the phosphorous atom to which $R^8$ and $R^9$ are linked, in which the rings are saturated, unsaturated and/or aromatic and in which one or more carbon atoms in said monocyclic or polycyclic ring system are optionally replaced with a heteromoiety selected from O, N, NH and $NC_{1-6}$alkyl.

In an embodiment of the disclosure, $R^8$ and $R^9$ are simultaneously $C_{1-6}$ alkyl or phenyl, in particular, methyl, ethyl, propyl, isopropyl, t-butyl, sec-butyl or phenyl. In further embodiments, $R^8$ and $R^9$ are simultaneously or independently isopropyl, t-butyl, or phenyl.

In another embodiment of the disclosure, $R^8$ and $R^9$ are linked to form an optionally substituted fused pentacyclic ring system having 23 atoms, including the phosphorous atom to which $R^8$ and $R^9$ are linked. In a further embodiment, the fused pentacyclic ring system is

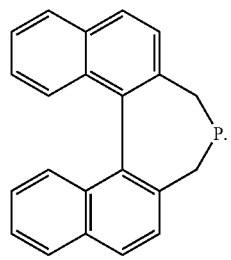

In another embodiment of the present disclosure, $R^{10}$ is selected from $C_{1-4}$alkyl, $C_{2-4}$alkenyl and phenyl, said latter 3 groups being optionally fluoro-substituted. In an embodiment, $R^{10}$ is selected from methyl and phenyl, said latter 2 groups being optionally fluoro-substituted.

According to other embodiments of the disclosure, the optional substituents are selected from one or more of halo, OH, $NH_2$, $OR^{11}$, $N(R^{11})_2$ and $R^{11}$, in which $R^{11}$ is selected from $C_{1-4}$alkyl, $C_{2-4}$alkenyl and phenyl, said latter 3 groups being optionally fluoro-substituted. In an embodiment, $R^{11}$ is selected from methyl and phenyl, said latter 2 groups being optionally fluoro-substituted.

In the present disclosure PG means a suitable protecting group. The term "suitable protecting group" would be understood by a person skilled in the art to means any moiety that, when linked to the amine functional group, prevents the amine functionality from participating in unwanted side reactions and which can be readily removed under conditions that do not degrade, decompose or otherwise interfere with the process of the disclosure to lower the yield and purity of the compounds of formula II. The selection of suitable protecting groups would be well within the abilities of a person skilled in the art. For example, a person skilled in the art may refer to "Protective Groups in Organic Chemistry" McOmie, J. F. W. Ed., Plenum Press, 1973 and in Greene, T. W. and Wuts, P. G. M., "Protective Groups in Organic Synthesis", John Wiley & Sons, $3^{rd}$ Edition, 1999. Examples of suitable protecting groups include, but are not limited to trimethylsilyl (TMS), acetyl, tert-butyldimethylsilyl (TBDMS), tert-butoxycarbonyl (BOC), benzyloxycarbonyl, 9-fluorenylmethyloxycarbonyl (FMOC), benzyl and the like.

In the present disclosure $LG^1$, means "leaving group". The term "suitable leaving group" as it applies to $LG^1$ would be understood by a person skilled in the art to mean any group attached to an atom that can be displaced by the nucleophilic phosphorus atom of the metal phosphide reagent under the conditions of the method of the disclosure. Suitable leaving groups for $LG^1$ include, but are not limited to, halides, including chloro, bromo, and iodo, tosylates, mesylates, and triflates and the like. In a further embodiment, $LG^1$ is a cyclic leaving group that is linked to another atom in the compound of formula I, including the nitrogen atom of the amine. In this latter instance, a portion of the leaving group remains linked to the other atom of the compound of formula I after nucleophilic displacement by the metal phosphide reagent, and those remaining portions may be removed, for example, during removal of the PG, to provide compounds of formula II. For example, a cyclic leaving group includes cyclic sulfamidates that are formed between the amine nitrogen and the carbon to which the $LG^1$ is attached.

In the present disclosure, Y is any suitable cation, for example any metal that can complex with a nucleophilic phosphide reagent. Such metals include the alkaline metals, for example lithium, sodium, potassium and the like, the alkaline earth metals. Suitable metals are the alkaline metals lithium, sodium and potassium. In embodiment of the disclosure, Y is Li or K.

In the present disclosure, p is 1 or 2, where when p is 1, the N atom is further linked to $R^7$ or any one of $R^1$, $R^2$, $R^3$, $R^4$, $R^5$, $R^6$ or $LG^1$, and when N is linked to any one of $R^1$, $R^2$, $R^3$, $R^4$, $R^5$, $R^6$ or $LG^1$, or if p is 2, q is 0. In an embodiment of the disclosure, p is 1 when a cyclic leaving group is used. In another embodiment, when p is 1, q is 1. In a further embodiment of the disclosure, p is 2 and the protecting group can be the same or different.

In an embodiment of the disclosure, the conditions to provide a compound of the formula II are nucleophilic reaction conditions that would be known to a person skilled in the art. In an embodiment of the method, the conditions to provide a compound of formula II comprise adding a compound of the formula I to a metal phosphide reagent of the formula Y—$PR^8R^9$, at a temperature of about −50° C. to about 0° C. over a period of about 1 hour to about 4 hours. In a further embodiment of the disclosure, the solution of a compound of the formula I and a metal phosphide reagent of the formula Y—$PR^8R^9$ is stirred at a temperature of about 10° C. to about 70° C. for a period of about 2 to about 24 hours. A person skilled in the art would understand that the conditions, including time and temperature may be varied, depending, for example, on the structure of the compound of formula I and the metal phosphide reagent.

In another embodiment of the disclosure, the conditions to provide a compound of the formula II comprise the reaction between the compound of the formula I and the metal phosphide reagent under anhydrous conditions and in an inert atmosphere (e.g. in the absence of oxygen).

In an embodiment of the method, the conditions to provide a compound of the formula II comprise the reaction between a compound of the formula I and a metal phosphide reagent in an aprotic solvent. In a subsequent embodiment of the method, the reaction between a compound of the formula I and a metal phosphide reagent is performed in a polar, aprotic solvent. In a further embodiment of the method, the reaction between a compound of the formula I and a metal phosphide reagent is performed in a variety of solvents, including ethers such as tetrahydrofuran or diethyl ether, acetonitrile, benzene, toluene, hexanes, dimethylformamide and the like. In a suitable embodiment of the method, the reaction between a compound of the formula I and a metal phosphide reagent is performed in tetrahydrofuran.

The compounds of formula I are commercially available or may be prepared using methods known in the art. For example, compounds of formula I may be prepared from the corresponding amino alcohols. Methods for attaching protecting groups onto amino groups are known in the art, in particular in the presence of a hydroxyl group or a latent or protected hydroxyl group (see for example, "Protective Groups in Organic Chemistry" McOmie, J. F. W. Ed., Plenum Press, 1973 and in Greene, T. W. and Wuts, P. G. M., "Protective Groups in Organic Synthesis", John Wiley & Sons, 3$^{rd}$ Edition, 1999). Conversions of hydroxyl groups into leaving groups are also well known in the art (see for example, "March's Advanced Organic Chemistry: Reactions, Mechanisms, and Structure, 5$^{th}$ Edition, December 2006, Smith M. B. and March, J. Authors, John Wiley & Sons, New Jersey, Publisher). In a specific example of the present disclosure, amino alcohols may be converted into a compound of formula I comprising a cyclic sulfamidate leaving group by first monoprotecting the amine nitrogen with any suitable PG, for example, t-butoxycarbonyl (t-BOC), followed by reaction of the resulting derivative according to the procedure described by Qin et al. (J. Org. Chem. 2004, 69:8533-8536), that is, with thionyl chloride (SOCl$_2$) under conditions to provide the cyclic sulfamidite which is converted to the corresponding sulfamidate by oxidation, for example with RuCl$_3$/NaIO$_4$. This method is depicted schematically in FIG. 1.

The metal phosphide reagents are either commercially available or may be prepared using methods known in the art as described hereinbelow. Typically the metal phosphide reagent is prepared in situ by reacting the corresponding phosphine, Z—PR$^8$R$^9$, where Z is for example, H or Cl, or the corresponding phosphepine borane, with a strong base, for example an alkyl lithium or lithium metal, at reduced temperatures, for example at about −80° C. to about 10° C.

In another embodiment, the method further comprises the step of reacting a compound of formula II as defined above, with a compound of the formula III

III

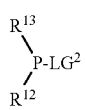

under conditions to provide a compound of the formula IV

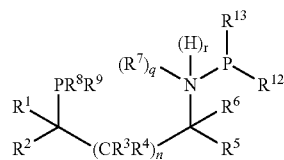

IV wherein R$^{12}$ and R$^{13}$ are as defined for R$^8$ and R$^9$ in formula II and R$^1$-R$^9$ are as defined in formula II, LG$^2$ is a suitable leaving group, and one of q and r is 1, while the other of q and r is 0.

In another embodiment, R$^{12}$ and R$^{13}$ are simultaneously or independently selected from H, C$_{1-10}$alkyl, C$_{2-10}$alkenyl, C$_{2-10}$alkynyl and aryl, said latter 4 groups being optionally substituted, or R$^{12}$ and R$^{13}$ are linked together to form an optionally substituted monocyclic or polycyclic ring system having 4 or more atoms, including the phosphorous atom to which R$^{12}$ and R$^{13}$ are linked, in which the rings are saturated, unsaturated and/or aromatic and in which one or more carbon atoms in said monocyclic or polycyclic ring system are optionally replaced with a heteromoiety selected from O, N, NH and NC$_{1-6}$alkyl. In a further embodiment, R$^{12}$ and R$^{13}$ are simultaneously or independently selected from H, C$_{1-6}$alkyl, C$_{2-6}$alkenyl, C$_{2-6}$alkynyl, phenyl, and naphthyl, said latter 5 groups being optionally substituted, or R$^{12}$ and R$^{13}$ are linked to form an optionally substituted monocylic, fused bicylic, fused tricyclic, fused quadracyclic, fused pentacyclic, fused hexacyclic or fused heptacyclic ring system having 4-32 atoms, including the phosphorous atom to which R$^{12}$ and R$^{13}$ are linked, in which the rings are saturated, unsaturated and/or aromatic and in which one or more carbon atoms in said monocyclic or polycyclic ring system are optionally replaced with a heteroatom selected from O, N, NH and NC$_{1-6}$alkyl. In another embodiment, the compound of formula III is

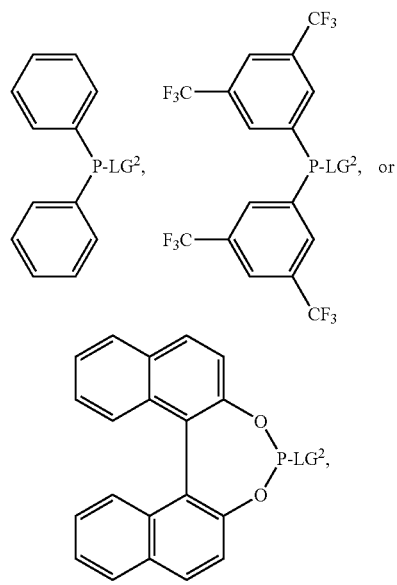

wherein LG$^2$ is a suitable leaving group.

In an embodiment of the disclosure, a method for preparing aminophosphine ligands comprising reacting a compound of the formula II

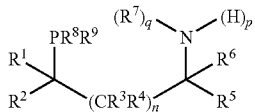

with a compound of the formula III

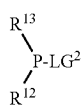

under conditions to provide a compound of the formula IV

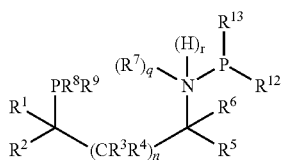

wherein
$LG^2$ is a suitable leaving group;
one of q and r is 1, while the other is 0;
n is 0, 1, 2, 3 or 4;
$R^1$ to $R^6$ are simultaneously or independently selected from H, $C_{1-20}$alkyl, $C_{2-20}$alkenyl, $C_{2-20}$alkynyl, $C_{3-20}$cycloalkyl, aryl and heteroaryl, said latter 6 groups being optionally substituted, or two adjacent or geminal groups, including the nitrogen atom of the amino group, are linked together to form an optionally substituted monocyclic or polycyclic, metalated, saturated, unsaturated and/or aromatic ring system having 3 or more atoms;
$R^7$ is selected from $C_{1-6}$alkyl and aryl, said latter two groups being optionally substituted;
$R^8$ and $R^9$ are simultaneously or independently selected from H, $C_{1-20}$alkyl, $C_{2-20}$alkenyl, $C_{2-20}$alkynyl, aryl, heteroaryl, $OR^{10}$ and $N(R^{10})_2$, said latter 7 groups being optionally substituted, or $R^8$ and $R^9$ are linked together to form an optionally substituted monocyclic or polycylic, saturated, unsaturated and/or aromatic ring system having 4 or more atoms, including the phosphorous atom to which said $R^8$ and $R^9$ groups are linked, and in which one or more carbon atoms in said monocyclic or polycyclic ring system are optionally replaced with a heteromoiety selected from O, S, N, NH and $NC_{1-6}$alkyl;
$R^{10}$ is selected from $C_{1-6}$alkyl, $C_{2-6}$alkenyl, $C_{2-6}$alkynyl and aryl, said latter 4 groups being optionally fluoro-substituted; the optional substituents are selected from one or more of halo, OH, $NH_2$, $OR^{11}$, $N(R^{11})_2$ and $R^{11}$;
$R^{11}$ is selected from $C_{1-6}$alkyl, $C_{2-6}$alkenyl, $C_{2-6}$alkynyl and aryl, said latter 4 groups being optionally fluoro-substituted; and
$R^{12}$ and $R^{13}$ are simultaneously or independently selected from H, $C_{1-20}$alkyl, $C_{2-20}$alkenyl, $C_{2-20}$alkynyl, aryl, heteroaryl, $OR^{10}$ and $N(R^{10})_2$, said latter 7 groups being optionally substituted, or $R^{12}$ and $R^{13}$ are linked together to form an optionally substituted monocyclic or polycylic, saturated, unsaturated and/or aromatic ring system having 4 or more atoms, including the phosphorous atom to which said $R^{12}$ and $R^{13}$ groups are linked, and in which one or more carbon atoms in said monocyclic or polycyclic ring system are optionally replaced with a heteromoiety selected from O, S, N, NH and $NC_{1-6}$alkyl.

In another embodiment, $R^1$ to $R^6$ are simultaneously or independently selected from H, $C_{1-10}$alkyl, $C_{2-10}$alkenyl, $C_{2-10}$alkynyl, $C_{3-10}$cycloalkyl, aryl and heteroaryl, said latter 6 groups being optionally substituted, or two adjacent or geminal groups, including the nitrogen atom of the amino group, are linked together to form an optionally substituted monocyclic or polycyclic, metallated, saturated, unsaturated and/or aromatic ring system having 5 or more atoms. In another embodiment, $R^1$ to $R^6$ are simultaneously or independently selected from H, $C_{1-4}$alkyl, $C_{2-4}$alkenyl, $C_{2-4}$alkynyl, $C_{3-6}$cycloalkyl, aryl and heteroaryl, said latter 6 groups being optionally substituted, or two adjacent or geminal groups, including the carbons to which these groups are attached and/or the nitrogen atom of the amino group, are linked together to form an optionally substituted monocyclic or polycyclic, metallated, saturated, unsaturated and/or aromatic ring system having 5 or more atoms. In a further embodiment, $R^1$ to $R^6$ are simultaneously or independently selected from H, methyl, or phenyl, or two adjacent or geminal groups, are linked together with the carbons to which said groups are attached, and/or with the nitrogen atom of the amino group, to form a phenyl, indanyl or ferrocenyl ring.

In another embodiment of the disclosure, n is equal to 0, 1 or 2. In a further embodiment, n is equal to 0 or 1.

In another embodiment of the disclosure, $R^7$ is selected from $C_{1-4}$alkyl or phenyl, said latter two groups being optionally substituted. In another embodiment, $R^7$ is methyl.

In a further embodiment of the disclosure, $R^8$ and $R^9$ are simultaneously or independently selected from H, $C_{1-10}$alkyl, $C_{2-10}$alkenyl, $C_{2-10}$alkynyl and aryl, said latter 4 groups being optionally substituted, or $R^8$ and $R^9$ are linked together to form an optionally substituted monocyclic or polycyclic ring system having 4 or more atoms, including the phosphorous atom to which $R^8$ and $R^9$ are linked, in which the rings are saturated, unsaturated and/or aromatic and in which one or more carbon atoms in said monocyclic or polycyclic ring system are optionally replaced with a heteromoiety selected from O, N, NH and $NC_{1-6}$alkyl. In another embodiment, $R^8$ and $R^9$ are simultaneously or independently selected from H, $C_{1-6}$alkyl, $C_{2-6}$alkenyl, $C_{2-6}$alkynyl, phenyl, and naphthyl, said latter 5 groups being optionally substituted, or $R^8$ and $R^9$ are linked to form an optionally substituted monocylic, fused bicylic, fused tricyclic, fused quadracyclic or fused pentacyclic ring system having 4-23 atoms, including the phosphorous atom to which $R^8$ and $R^9$ are linked, in which the rings are saturated, unsaturated and/or aromatic and in which one or more carbon atoms in said monocyclic or polycyclic ring system are optionally replaced with a heteromoiety selected from O, N, NH and $NC_{1-6}$alkyl. In a further embodiment, $R^8$ and $R^9$ are simultaneously or independently isopropyl, t-butyl, or phenyl. In another embodiment of the disclosure, $R^8$ and $R^9$ are linked to form an optionally substituted fused pentacyclic ring system having 23 atoms, including the phosphorous atom to which $R^8$ and $R^9$ are linked. In a further embodiment, wherein the fused pentacyclic ring system is

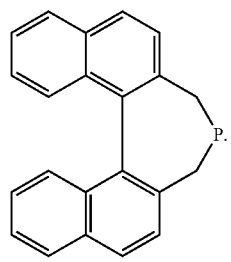

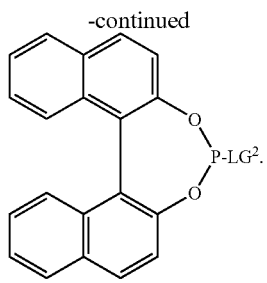

In the present disclosure, $R^{10}$ is selected from $C_{1-4}$alkyl, $C_{2-4}$alkenyl and phenyl, said latter 3 groups being optionally fluoro-substituted. In an embodiment, $R^{10}$ is selected from methyl and phenyl, said latter 2 groups being optionally fluoro-substituted.

In embodiments of the disclosure, the optional substituents are selected from one or more of halo, OH, $NH_2$, $OR^{11}$, $N(R^{11})_2$ and $R^{11}$, in which $R^{11}$ is selected from the group consisting of $C_{1-4}$alkyl, $C_{2-4}$alkenyl and phenyl, said latter 3 groups being optionally fluoro-substituted. In an embodiment, $R^{11}$ is selected from methyl and phenyl, said latter 2 groups being optionally fluoro-substituted.

In another embodiment, $R^{12}$ and $R^{13}$ are simultaneously or independently selected from H, $C_{1-10}$alkyl, $C_{2-10}$alkenyl, $C_{2-10}$alkynyl and aryl, said latter 4 groups being optionally substituted, or $R^{12}$ and $R^{13}$ are linked together to form an optionally substituted monocyclic or polycyclic ring system having 4 or more atoms, including the phosphorous atom to which $R^{11}$ and $R^{12}$ are linked, in which the rings are saturated, unsaturated and/or aromatic and in which one or more carbon atoms in said monocyclic or polycyclic ring system are optionally replaced with a heteromoiety selected from O, N, NH and $NC_{1-6}$alkyl. In a further embodiment, $R^{12}$ and $R^{13}$ are simultaneously or independently selected from H, $C_{1-6}$alkyl, $C_{2-6}$alkenyl, $C_{2-6}$alkynyl, phenyl, and naphthyl, said latter 5 groups being optionally substituted, or $R^{12}$ and $R^{13}$ are linked to form an optionally substituted monocylic, fused bicylic, fused tricyclic, fused quadracyclic, fused pentacyclic, fused hexacyclic or fused heptacyclic ring system having 4-32 atoms, including the phosphorous atom to which $R^{12}$ and $R^{13}$ are linked, in which the rings are saturated, unsaturated and/or aromatic and in which one or more carbon atoms in said monocyclic or polycyclic ring system are optionally replaced with a heteroatom selected from O, N, NH and $NC_{1-6}$alkyl. In another embodiment, the compound of formula III is

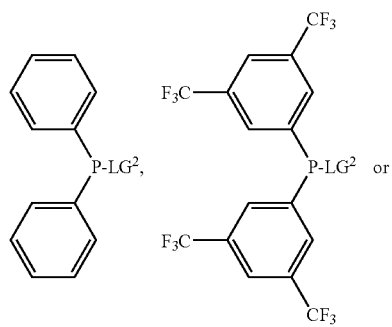

In the present disclosure $LG^2$ in a compound of formula III, is a suitable leaving group. The term "suitable leaving group" in a compound of formula III would be understood by a person skilled in the art to mean any group attached to a phosphorous atom that can be displaced by the nucleophilic nitrogen atom of the compound of formula II. Suitable leaving groups include, but are not limited to, halides, including chloro, bromo, and iodo, tosylates, mesylates, and triflates and the like.

In an embodiment of the disclosure, the conditions to provide a compound of the formula IV are nucleophilic reaction conditions that would be known to a person skilled in the art. In an embodiment of the method, the conditions to provide a compound of formula IV comprise adding a compound of the formula III to a compound of the formula II at about room temperature. In a further embodiment of the disclosure, the solution of a compound of the formula II and formula III is stirred at about room temperature for a period of about 2 to about 24 hours. A person skilled in the art would understand that the conditions, including time and temperature may be varied, depending, for example, on the structure of the compounds of formula II and formula III.

In another embodiment of the disclosure, the conditions to provide a compound of the IV comprise the reaction between the compound of the formula II and a compound of formula III under anhydrous conditions and in an inert atmosphere (e.g. in the absence of oxygen).

In an embodiment of the method, the conditions to provide a compound of the formula IV comprise the reaction between a compound of the formula II and a compound of the formula III in an aprotic solvent. In a subsequent embodiment of the method, the reaction between a compound of the formula II and a compound of the formula III is performed in a polar, aprotic solvent. In a further embodiment of the method, the reaction between a compound of the formula II and a compound of the formula III is performed in a variety of solvents, including chlorinated solvents such as dichloromethane, ethers such as tetrahydrofuran or diethyl ether, acetonitrile, benzene, toluene, hexanes, dimethylformamide and the like. In a suitable embodiment of the method, the reaction between a compound of the formula II and a compound of the formula III is performed in dichloromethane.

In an embodiment of the disclosure, the aminophosphine ligands prepared using the method of the present disclosure are complexed with any metal for use as catalysts. In an embodiment of the invention, the metal is any transition metal of groups 3 through 12 of the periodic table, suitably groups 4 through 10, plus the lanthanides and actinides. Examples of suitable metals include, but are not limited to Co, Rh, Ir, Ru, Os and Re. In an embodiment of the disclosure, the metal is Ru. In a further embodiment of the disclosure, the aminophosphine ligands of formula II are complexed with an $RuCl_2$ group to form $RuCl_2$(aminophosphine)$_2$ and $RuCl_2$(diphosphine)(aminophosphine) catalysts.

In another embodiment of the disclosure, the aminophosphine metal catalysts are those useful for the hydrogenation of ketones, aldehydes and imines.

In a further embodiment of the disclosure, there is included novel aminophosphepine ligands of the formula V

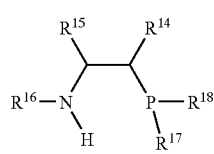

wherein
$R^{14}$ and $R^{15}$ are simultaneously or independently selected from H, $C_{1-20}$alkyl, $C_{2-20}$alkenyl, $C_{2-20}$alkynyl, $C_{3-20}$cycloalkyl, aryl and heteroaryl, said latter 6 groups being optionally substituted;
$R^{16}$ is selected from H, $C_{1-6}$alkyl and aryl, said latter two groups being optionally substituted or $R^{16}$ is $PR^{19}R^{20}$;
or two of $R^{14}$, $R^{15}$ and $R^{16}$ are linked to form an optionally substituted monocyclic or polycyclic, metalated, saturated, unsaturated and/or aromatic ring system having 3 or more atoms;
$R^{17}$ and $R^{18}$ are linked together with the phosphorous atom to which said $R^{17}$ and $R^{18}$ groups are linked to form an optionally substituted polycyclic ring of the formula

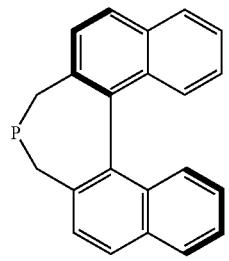

in which one or more carbon atoms in said polycyclic ring system are optionally replaced with a heteromoiety selected from O, S, N, NH and $NC_{1-6}$alkyl;
$R^{19}$ and $R^{20}$ are simultaneously or independently selected from H, $C_{1-20}$alkyl, $C_{2-20}$alkenyl, $C_{2-20}$alkynyl, aryl, heteroaryl, $OR^{21}$ and $N(R^{21})_2$, said latter 7 groups being optionally substituted, or $R^{19}$ and $R^{20}$ are linked together to form an optionally substituted monocyclic or polycylic, saturated, unsaturated and/or aromatic ring system having 4 or more atoms, including the phosphorous atom to which said $R^{19}$ and $R^{20}$ groups are linked, and in which one or more carbon atoms in said monocyclic or polycyclic ring system are optionally replaced with a heteromoiety selected from O, S, N, NH and $NC_{1-6}$alkyl;
the optional substituents are selected from one or more of halo, OH, $NH_2$, $OR^{22}$, $N(R^{22})_2$ and $R^{22}$; and
$R^{21}$ and $R^{22}$ are independently selected from $C_{1-6}$alkyl, $C_{2-6}$alkenyl, $C_{2-6}$alkynyl and aryl, said latter 4 groups being optionally fluoro-substituted.

In another embodiment of the disclosure, $R^{14}$ and $R^{15}$ are simultaneously or independently selected from H, $C_{1-10}$alkyl, $C_{2-10}$alkenyl, $C_{2-10}$alkynyl, $C_{3-10}$-cycloalkyl, aryl and heteroaryl, said latter 6 groups being optionally substituted. In a further embodiment, $R^{14}$ and $R^{15}$ are simultaneously or independently selected from H, $C_{1-4}$alkyl, $C_{2-4}$alkenyl, $C_{2-4}$alkynyl, $C_{3-6}$cycloalkyl, aryl and heteroaryl, said latter 6 groups being optionally substituted. In another embodiment, $R^{14}$ and $R^{15}$ are simultaneously or independently selected from H, methyl, or phenyl.

In another embodiment of the disclosure, $R^{16}$ is H, $C_{1-4}$alkyl or phenyl, said latter two groups being optionally substituted. In a further embodiment, $R^{16}$ is H or methyl.

In yet another embodiment, $R^{16}$ is $PR^{19}R^{20}$, where $R^{19}$ and $R^{20}$ are simultaneously or independently selected from H, $C_{1-10}$alkyl, $C_{2-10}$alkenyl, $C_{2-10}$alkynyl, aryl, heteroaryl, $OR^{21}$ and $N(R^{21})_2$, said latter 7 groups being optionally substituted, or $R^{19}$ and $R^{20}$ are linked together to form an optionally substituted monocyclic or polycylic, saturated, unsaturated and/or aromatic ring system having 5 to 23 atoms, including the phosphorous atom to which said $R^{19}$ and $R^{20}$ groups are linked, and in which one or more carbon atoms in said monocyclic or polycyclic ring system are optionally replaced with a heteromoiety selected from O, S, N, NH and $NC_{1-4}$alkyl. In a further embodiment, $R^{19}$ and $R^{20}$ are simultaneously or independently selected from H, $C_{1-6}$alkyl, phenyl and $OR^{21}$, said latter 3 groups being optionally substituted, or $R^{19}$ and $R^{20}$ are linked together to form an optionally substituted monocyclic or polycyclic, saturated, unsaturated and/or aromatic ring system having 5 to 23 atoms, including the phosphorous atom to which said $R^{19}$ and $R^{20}$ groups are linked, and in which one or more carbon atoms in said monocyclic or polycyclic ring system are optionally replaced with O. In yet another embodiment $R^{16}$ is selected from:

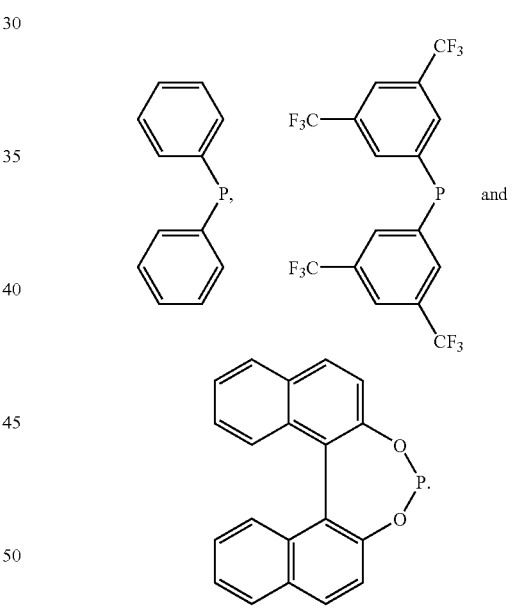

In another embodiment, two of $R^{14}$, $R^{15}$ and $R^{16}$ are linked to form an optionally substituted monocyclic, bicyclic, tricyclic, saturated, unsaturated and/or aromatic ring system having 5 to 14 atoms. In a further embodiment, $R^{15}$ and $R^{16}$ are linked to form an optionally substituted monocyclic or bicyclic, saturated, and/or aromatic ring system having 5 to 10 atoms.

In a further embodiment of the disclosure the optional substituents on the compounds of formula V are selected from one or more of Cl, F, $OR^{22}$ and $N(R^{22})_2$ and $R^{22}$, where $R^{22}$ is selected from $C_{1-6}$alkyl, and phenyl, said latter 4 groups being optionally fluoro-substituted. In yet another embodiment, the optional substituents on the compounds of formula V are selected from one or more of $CH_3$, $CF_3$, $OCH_3$, and $OCF_3$.

In yet another embodiment of the present disclosure, the stereochemistry of the compounds of formula V is as follows:

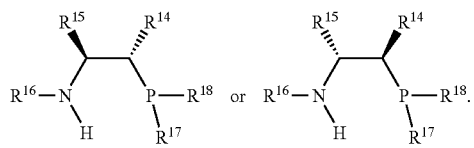

In an embodiment of the disclosure, there is included a novel aminophosphine ligand of the Formulae VI or VII

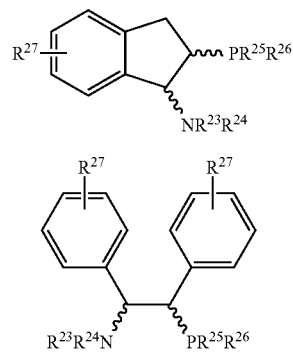

wherein
R$^{23}$ and R$^{24}$ are simultaneously or independently selected from H, C$_{1-6}$alkyl and aryl, said latter two groups being optionally substituted or one of R$^{23}$ and R$^{24}$ is PR$^{28}$R$^{29}$;
R$^{25}$ and R$^{26}$ are simultaneously or independently selected from H, C$_{1-20}$alkyl, C$_{2-20}$alkenyl, C$_{2-20}$alkynyl, aryl, heteroaryl, OR$^{30}$ and N(R$^{30}$)$_2$, said latter 7 groups being optionally substituted, or R$^{25}$ and R$^{26}$ are linked together to form an optionally substituted monocyclic or polycyclic, saturated, unsaturated and/or aromatic ring system having 4 or more atoms, including the phosphorous atom to which said R$^{25}$ and R$^{26}$ groups are linked, and in which one or more carbon atoms in said monocyclic or polycyclic ring system are optionally replaced with a heteromoiety selected from O, S, N, NH and NC$_{1-6}$alkyl;
R$^{27}$ represents optional substituents selected from one or more of OH, NH$_2$, OR$^{31}$, N(R$^{31}$)$_2$ and R$^{31}$, alternatively, R$^{27}$ is H;
R$^{28}$ and R$^{29}$ are simultaneously or independently selected from H, C$_{1-20}$alkyl, C$_{2-20}$alkenyl, C$_{2-20}$alkynyl, aryl, heteroaryl, OR$^{32}$ and N(R$^{32}$)$_2$, said latter 7 groups being optionally substituted, or R$^{28}$ and R$^{29}$ are linked together to form an optionally substituted monocyclic or polycyclic, saturated, unsaturated and/or aromatic ring system having 4 or more atoms, including the phosphorous atom to which said R$^{28}$ and R$^{29}$ groups are linked, and in which one or more carbon atoms in said monocyclic or polycyclic ring system are optionally replaced with a heteromoiety selected from O, S, N, NH and NC$_{1-6}$alkyl;
R$^{30}$, R$^{31}$ and R$^{32}$ are independently selected from C$_{1-6}$alkyl, C$_{2-6}$alkenyl, C$_{2-6}$alkynyl and aryl, said latter 4 groups being optionally fluoro-substituted;
the optional substituents are selected from one or more of halo, OH, NH$_2$, OR$^{33}$, N(R$^{33}$)$_2$ and R$^{33}$; and
R$^{33}$ is selected from C$_{1-6}$alkyl, C$_{2-6}$alkenyl, C$_{2-6}$alkynyl and aryl, said latter 4 groups being optionally fluoro-substituted.

In an embodiment of the disclosure, R$^{23}$ and R$^{24}$ are simultaneously or independently selected from H, C$_{1-4}$alkyl, phenyl and naphthyl. In yet another embodiment, R$^{23}$ and R$^{24}$ are simultaneously or independently selected from H, methyl and phenyl. In yet another embodiment, R$^{23}$ and R$^{24}$ are simultaneously selected from H, methyl and phenyl.

In yet another embodiment, one of R$^{23}$ and R$^{24}$ is PR$^{28}$R$^{29}$ and R$^{28}$ and R$^{29}$ are simultaneously or independently selected from H, C$_{1-10}$alkyl, C$_{2-10}$alkenyl, C$_{2-20}$alkynyl, aryl, heteroaryl, OR$^{32}$ and N(R$^{32}$)$_2$, said latter 7 groups being optionally substituted, or R$^{28}$ and R$^{29}$ are linked together to form an optionally substituted monocyclic or polycyclic, saturated, unsaturated and/or aromatic ring system having 5 or more atoms, including the phosphorous atom to which said R$^{28}$ and R$^{29}$ groups are linked, and in which one or more carbon atoms in said monocyclic or polycyclic ring system are optionally replaced with a heteromoiety selected from O, S, N, NH and NC$_{1-6}$alkyl. In a further embodiment, R$^{28}$ and R$^{29}$ are simultaneously or independently selected from H, C$_{1-6}$alkyl, phenyl and OR$^{32}$, said latter 3 groups being optionally substituted, or R$^{28}$ and R$^{29}$ are linked together to form an optionally substituted monocyclic or polycyclic, saturated, unsaturated and/or aromatic ring system having 5 to 23 atoms, including the phosphorous atom to which said R$^{28}$ and R$^{29}$ groups are linked, and in which one or more carbon atoms in said monocyclic or polycyclic ring system are optionally replaced with O. In yet another embodiment PR$^{28}$R$^{29}$ is selected from:

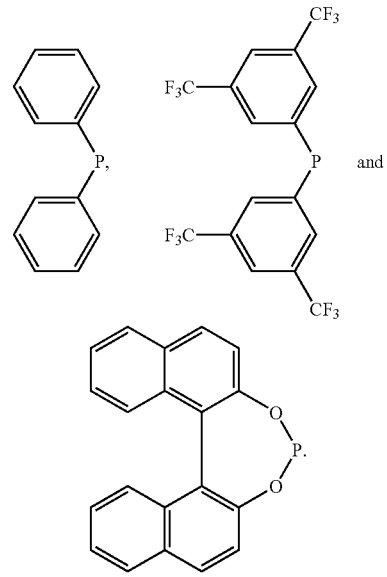

In further embodiments of the present disclosure, R$^{25}$ and R$^{26}$ are simultaneously or independently selected from H, C$_{1-10}$alkyl, C$_{2-10}$alkenyl, C$_{2-10}$alkynyl, aryl, heteroaryl, OR$^{30}$ and N(R$^{30}$)$_2$, said latter 7 groups being optionally substituted, or R$^{25}$ and R$^{26}$ are linked together to form an optionally substituted monocyclic or polycyclic, saturated, unsaturated and/or aromatic ring system having 5 or more atoms, including the phosphorous atom to which said R$^{25}$ and R$^{26}$ groups are linked, and in which one or more carbon atoms in said monocyclic or polycyclic ring system are optionally replaced with a heteromoiety selected from O, S, N, NH and NC$_{1-6}$alkyl. In a further embodiment, R$^{25}$ and R$^{26}$ are simultaneously or independently selected from H, C$_{1-6}$alkyl, phenyl and OR$^{30}$, said latter 3 groups being optionally substituted, or R$^{25}$ and R$^{26}$ are linked together to form an optionally substituted monocyclic or polycylic, saturated, unsaturated and/or aromatic ring system having 5 to 23 atoms, including the phosphorous atom to which said R²⁵ and R²⁶ groups are linked, and in which one or more carbon atoms in said monocyclic or polycyclic ring system are optionally replaced with O.

In an embodiment of the disclosure R²⁷ represents optional substituents selected from one or five of OR³¹, N(R³¹)₂ and R³¹ is independently selected from C₁₋₄alkyl and phenyl, said latter 2 groups being optionally fluoro-substituted. In a further embodiment, R²⁷ is H.

In further embodiments of the disclosure, R³⁰ and R³² are independently selected from C₁₋₄alkyl, and phenyl, said latter 2 groups being optionally fluoro-substituted.

In other embodiments if the present disclosure, the optional substituents are selected from one or five of Cl, F, OR³³, N(R³³)₂ and R³³, and R³³ is selected from C₁₋₄alkyl and phenyl, said latter 2 groups being optionally fluoro-substituted.

In a further embodiment of the present disclosure, the amino phosphine ligand of the formula V is

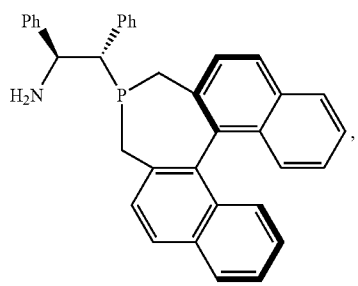

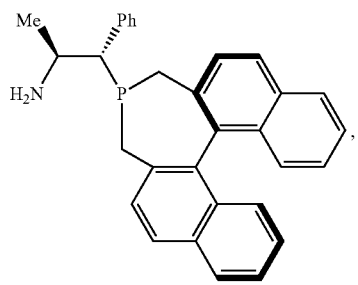

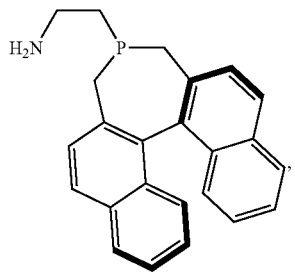

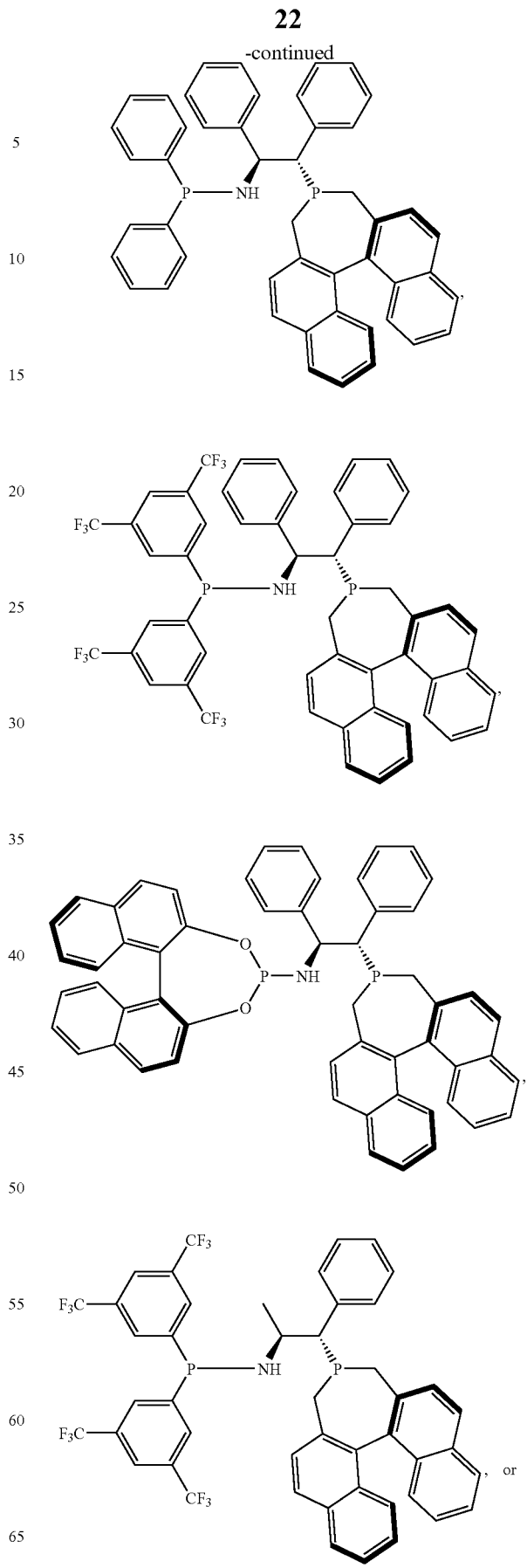

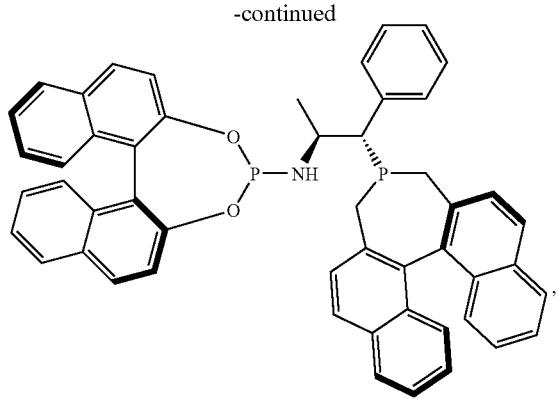

or the compounds as shown above, substituted on the naphthyl, phenyl or alkyl groups by one or more, suitably one or three, more suitably one or two substituents independently selected from F, Cl, $C_{1-4}$alkyl, $OCF_3$ and $OC_{1-4}$alkyl.

In another embodiment of the disclosure, the aminophosphine ligand of formula VI is

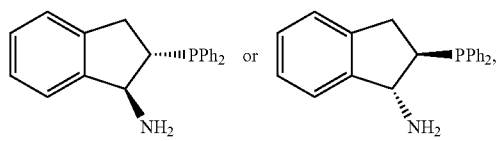

or the compounds as shown above, substituted on the naphthyl, phenyl or alkyl groups by one or more, suitably one or three, more suitably one or two substituents independently selected from F, Cl, $C_{1-4}$alkyl, $OCF_3$ and $OC_{1-4}$alkyl.

In another embodiment, the aminophosphine ligand of formula VII is

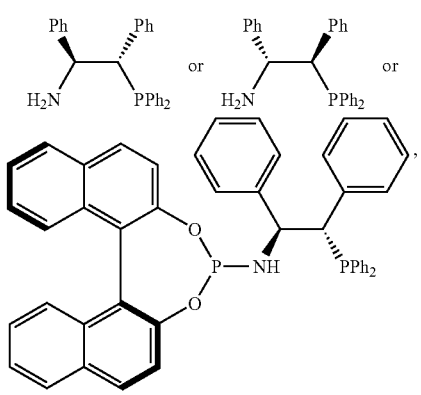

or the compounds as shown above, substituted on the naphthyl, phenyl or alkyl groups by one or more, suitably one or three, more suitably one or two substituents independently selected from F, Cl, $C_{1-4}$alkyl, $OCF_3$ and $OC_{1-4}$alkyl.

Also included as embodiments of the present disclosure are metal complexes, suitably a transition metal complex comprising a ligand of the formula II, IV, V, VI or VII. In particular the transition metal complex is of the type $MCl_2$(aminophosphine)$_2$ and $MCl_2$(diphosphine)(aminophosphine), where aminophosphine is of the formula IIa, IIb, IIc or IId. Suitably M is Ru.

The following non-limiting examples are illustrative of the present disclosure:

EXAMPLES

All preparations and manipulations were carried out under hydrogen or argon atmospheres with the use of standard Schlenk, vacuum line and glove box techniques in dry, oxygen-free solvents. Tetrahydrofuran (THF), diethyl ether ($Et_2O$) and hexanes were purified and dried using an Innovative Technologies solvent purification system. Deuterated solvents were degassed and dried before use. Precursor chemicals were supplied by Aldrich Chemical Company, Dalchem, Digital Specialty Chemicals and ChemPacific. NMR spectra were recorded on either a Varian Unity Inova 300 MHz spectrometer (300 MHz for $^1H$, 75 MHz for $^{13}C$ and 121.5 for $^{31}P$) or a Bruker Avance 500 MHz DRX spectrometer. All $^{31}P$ chemical shifts were measured relative to 85% $H_3PO_4$ as an external reference. The $^1H$ and $^{13}C$ chemical shifts were measured relative to partially deuterated solvent peaks but are reported relative to tetramethylsilane. The alcohol products obtained from the catalytic hydrogenation of ketones were characterized by their $^1H$ and $^{13}C$ NMR spectra.

Example 1

Preparation of Aminophosphine Ligands

Example 1.1

2-(Diphenylphosphino)ethanamine

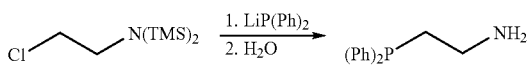

Butyl lithium (155 ml of a 1.6 M solution in hexane) was added dropwise to a cold (0° C.) solution of diphenylphosphine (45 g, 0.24 mole) in THF (200 ml). The mixture was stirred for 2 hours at room temperature and a solution of N,N'-bis(trimethylsilyl)-2-chloroethanamine (54 g, 0.24 mole) added slowly at 0° C. The mixture was refluxed for 4 hours then cooled to room temperature. Water (50 ml) was added, followed by 2.0 M $H_2SO_4$ solution (200 ml). After stirring for 1 hour at room temperature a solution of 4.0 M NaOH solution (220 ml) was then added, and the mixture stirred for 1 hour. Hexane (200 ml) was added and the aqueous phase was separated and removed. The organic layer was dried ($Na_2SO_4$), filtered through a pad of silica gel, and evaporated to yield the aminophosphine, which was purified by vacuum distillation. Yield=52.3 g. $^1H$ NMR($C_6D_6$): δ 7.72-7.32 (m, 10H), 2.95 (quartet, 2H, $CH_2$), 2.26 (triplet, 2H, $CH_2$), 0.92 (br, 2H, $NH_2$). $^{31}P$ NMR($C_6D_6$): δ −23.3 (s).

Example 1.2

2-(Diisopropylphosphino)ethanamine

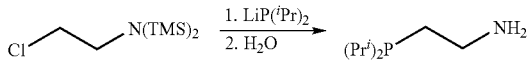

A THF (100 ml) solution of chlorodiisopropylphosphine (30 g, 0.20 mole) was added dropwise to a suspension of lithium granules (5.0 g, 0.72 mol) in THF (100 ml) maintained at room temperature, and the mixture stirred for 72 hours. The mixture was filtered and the filtrate cooled to 0° C. and a solution of N,N'-bis(trimethylsilyl)-2-chloroethanamine (44.2 g, 0.20 mole) added slowly. The mixture was refluxed for 4 hours then cooled to room temperature. Water (50 ml) was added, followed by 2.0 M $H_2SO_4$ solution (160 ml). After stirring for 1 hour at room temperature a solution of 4.0 M NaOH solution (180 ml) was then added, and the mixture stirred for 1 hour. Hexane (200 ml) was added and the aqueous phase was separated and removed. The organic layer was dried ($Na_2SO_4$), filtered through a pad of silica gel, and evaporated to yield the aminophosphine, which was purified by vacuum distillation. Yield=28.2 g. $^1H$ NMR($C_6D_6$): δ 2.71 (m, 2H, $CH_2$), 1.52 (doublet of septet, 2H, CH), 1.31 (m, 2H, $CH_2$), 0.96 (m, 12H, $CH_3$), 0.90 (br, 2H, $NH_2$). $^{31}P$ NMR ($C_6D_6$): δ −5.6 (s).

Example 1.3

2-(Di-tert-butylphosphino)ethanamine

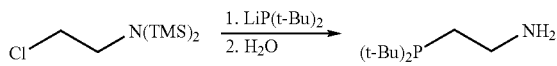

A THF (100 ml) solution of chlorodi-tert-butylphosphine (42 g, 0.23 mole) was added dropwise to a suspension of lithium granules (5.0 g, 0.72 mol) in THF (100 ml) maintained at room temperature, and the mixture stirred for 72 hours. The mixture was filtered and the filtrate cooled to 0° C. and a solution of N,N'-bis(trimethylsilyl)-2-chloroethanamine (51.7 g, 0.23 mole) added slowly. The mixture was refluxed for 4 hours then cooled to room temperature. Water (50 ml) was added, followed by 2.0 M $H_2SO_4$ solution (200 ml). After stirring for 1 hour at room temperature a solution of 4.0 M NaOH solution (220 ml) was then added, and the mixture stirred for 1 hour. Hexane (200 ml) was added and the aqueous phase was separated and removed. The organic layer was dried ($Na_2SO_4$), filtered through a pad of silica gel, and evaporated to yield the aminophosphine, which was purified by vacuum distillation. Yield=40.3 g. $^1H$ NMR($C_6D_6$): δ 2.76 (m, 2H, $CH_2$), 1.35 (m, 2H, $CH_2$), 1.02 (d, 18H, $CH_3$), 0.84 (br, 2H, $NH_2$). $^{31}P$ NMR($C_6D_6$): δ 17.5 (s).

Preparation of Aminophosphine Ligands from Amino Alcohols

Example 2

General Procedures for the Preparation of N-tert-butoxycarbonylamino Alcohol

A solution of $(Boc)_2O$ (44 mmol) in THF (50 ml) was added to the mixture of the amino alcohol (40 mmol) and sodium carbonate (80 mmol) in THF/$H_2O$ (1/1, 300 ml) at 0° C. The mixture was stirred at 0° C. for 1 h and then at room temperature for another two 2 h (TLC was used to monitor the reactions). Water (200 ml) was added to the mixture upon completion. The organic layer was separated and the aqueous layer was extracted with ethyl acetate (200 ml). The combined organic layers was washed with brine (300 ml) and dried with anhydrous $MgSO_4$ for 1 h. It was then filtered and the solvent was removed under vacuum to give the product (yield=90-99%). It was sufficiently pure for the next step. The pure product was obtained by recrystallization from the THF and hexane, or by purification with silica gel chromatography.

Example 2.1

Tert-butyl(1S,2R)-2-hydroxy-1,2-diphenylethylcarbamate

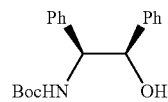

Yield: 90%. $^1H$ NMR ($CD_2Cl_2$): δ 7.25-7.27 (m, 6H), 7.08-7.11 (m, 4H), 5.33 (m, 1H), 5.04 (m, 1H), 4.92 (b, 1H), 2.60 (b, 1H), 1.38 (s, 9H).

Example 2.2

Tert-butyl(1S,2R)-2-hydroxy-1-phenylpropylcarbamate

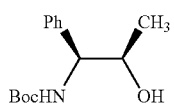

Yield: 98%. $^1H$ NMR ($CD_2Cl_2$): δ 7.34-7.36 (m, 5H), 4.80-4.82 (m, 2H), 3.94 (b, 1H), 3.60 (b, 1H), 1.45 (s, 9H), 9.70 (d, J=6.9 Hz, 3H).

Example 2.3

Tert-butyl(1R,2S)-2-methyl-1-hydroxy-1-phenylethylcarbamate

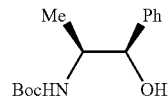

Yield: quantitative yield. $^1H$ NMR ($CDCl_3$) δ 7.27-7.35 (m, 5H), 4.85 (d, 1H), 4.62 (b, 1H), 3.99 (b, 1H), 3.24 (b, 1H), 1.46 (s, 9H), 0.99 (d, J=6.9 Hz, 3H).

Example 2.4

Tert-butyl(1S,2R)-2-hydroxy-2,3-dihydro-1H-inden-1-ylcarbamate

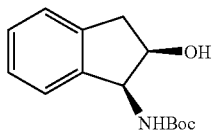

Yield: 98%. $^1$H NMR (CD$_2$Cl$_2$) δ 7.49 (d, 1H), 7.25-7.28 (m. 3H), 5.64 (d, J=5.4 Hz, 1H), 5.44 (m, 1H), 3.30 (b, 2H), 1.53 (s, 9H).

Example 3

General Procedure for the Preparation of Sulfamidates

An aliquot of SOCl$_2$ (30 mmol) was added to the solution of N-alkoxycarbonylamino alcohol (30 mmol) and dimethylaminopyridine (DMAP, 90 mmol) in CH$_2$Cl$_2$ (200 ml) at −45° C. The reaction was stirred at −45° C. for 1-2 h and then water (2 ml) was added to quench the reaction. Another potion of water (150 ml) was added and the mixture was stirred at RT for 30 min. The organic layer was separated and the aqueous layer was extracted with CH$_2$Cl$_2$ (100 ml×2). The combined organic layers was washed with water (150 ml×2) and dried with anhydrous MgSO$_4$. It was filtered through a silica gel pad (eluent: CH$_2$Cl$_2$). The filtration was dried under vacuum to give the sulfamidite which was sufficiently pure to be used for the next step without further purification.

To an ice-cold solution of the sulfamidite in a mixture of CH$_3$CN (80 ml), CH$_2$Cl$_2$ (20 ml) and water (80 ml) was added ruthenium(III) chloride (20 mg) and NaIO$_4$ (40 mmol). The mixture was stirred at 0° C. for 2-4 h (TLC was used to monitor the reactions), and water (50 ml) was added. The organic layer was separated and the aqueous phase was extracted with ether (60 ml×2). The combined organic layers was washed with brine (150 ml×2) and dried with anhydrous MgSO$_4$. It was filtered and the solvent was removed to give the crude product which was purified by recrystallization (THF/hexane) or by silica gel flash chromatography. The overall yield for the two steps was 40-60%.

Example 3.1

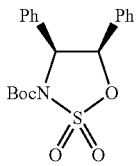

The overall yield for the two steps is 86%. $^1$H NMR (CD$_2$Cl$_2$) δ 7.14-7.24 (m, 6H), 7.06-7.10 (m, 2H), 6.95-7.00 (m, 2H), 6.20 (d, J=5.6 Hz, 1H), 5.45 (b, J=5.6 Hz, 1H), 1.46 (s, 9H).

Example 3.2

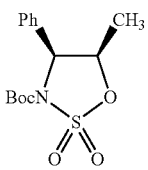

Yield: 50%. $^1$H NMR (CD$_2$Cl$_2$): δ 7.36-7.47 (m, 3H), 7.33-7.35 (m, 2H), 5.99 (d, J=5.1 Hz, 1H), 4.59 (dq, J=5.1 Hz, J=6.5 Hz, 1H), 1.57 (s, 9H), 1.06 (d, J=6.4 Hz, 3H).

Example 3.3

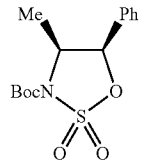

Yield: 34%, two steps. $^1$H NMR (CDCl$_3$) δ 7.42-7.45 (m, 3H), 7.30-7.33 (m, 2H), 5.96 (d, J=5.2 Hz, 1H), 4.52-4.62 (m, 1H), 1.58 (s, 9H), 1.08 (d, J=6.6 Hz, 3H).

Example 3.4

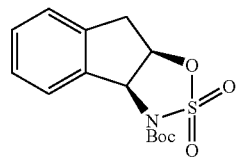 [SMILES: CC(C)(C)OC(=O)N1[C@H]2c3ccccc3C[C@H]2OS1(=O)=O]

Yield: 40%, two steps. $^1$H NMR (CD$_2$Cl$_2$) δ 7.49 (d, 1H), 7.25-7.28 (m. 3H), 5.64 (d, J=5.4 Hz, 1H), 5.44 (m, 1H), 3.30 (b, 2H), 1.53 (s, 9H).

Example 4

General Procedures for the Preparation of Aminophosphine Ligands from Sulfamidates A solution of potassium diphenylphosphide (28 ml, 0.5 M in hexane, 14 mmol) was added slowly to a solution of the sulfamidate (12 mmol) in THF (100 ml) at −50° C. and the mixture was stirred at that temperature for 2 h, then the mixture was slowly warmed to RT and stirred overnight. De-gassed H$_2$SO$_4$ solution (2M, 30 ml) in brine (50 ml) was added and the mixture was stirred for 1 h, after which, de-gassed saturated Na$_2$CO$_3$ solution (50 ml) was added to neutralize the acid. The organic layer was separated and the aqueous layer was extracted with CH$_2$Cl$_2$ (100 ml). The combined organic layer was washed with brine and dried with anhydrous MgSO$_4$. It was filtered and the solvent was removed under vacuum to give the crude product as a viscous oil which was dissolved in CH$_2$Cl$_2$ (50 ml). To the ice-cooled solution CF$_3$CO$_2$H (20 ml) was added and the mixture was stirred at RT overnight. All the volatiles were removed under vacuum and the residue was neutralized with de-gassed saturated Na$_2$CO$_3$ solution (50 ml). The product was extracted with CH$_2$Cl$_2$ (100 ml×2). The combined organic layers was washed with brine and dried with anhydrous MgSO$_4$. It was filtered with a silica gel pad (eluent: CH$_2$Cl$_2$ to remove impurities, then CH$_2$Cl$_2$/THF to elute the product). The solvent was removed to give the pure aminophosphine product. The yields are 85-90%.

Example 4.1

(1S,2S)-2-(Diphenylphosphino)-1,2-diphenyletha-namine

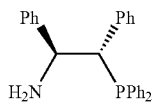

Yield=85%. $^1$H NMR (CD$_2$Cl$_2$) δ 7.81-7.88 (m, 2H), 7.42-7.50 (m, 3H), 6.88-7.22 (m, 15H), 4.43 (dd, 1H), 4.05 (dd, 1H), 1.6 (b, 2H), $^{31}$P NMR (CD$_2$Cl$_2$) δ −7.15 ppm.

Example 4.2

(1R,2R)-2-(Diphenylphosphino)-1,2-diphenyletha-namine

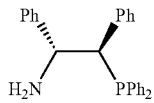

The $^1$H NMR spectrum for this compound was similar to that of (1S,2S)-2-(diphenylphosphino)-1,2-diphenyletha-namine (Example 4.1).

Example 4.3

(1S,2S)-2-(Diphenylphosphino)-2,3-dihydro-1H-inden-1-amine

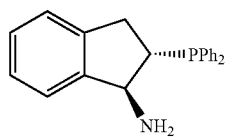

Yield=87%. $^1$H NMR (CD$_2$Cl$_2$): δ 7.54-7.66 (m, 4H), 7.38-7.42 (m, 6H), 7.26-7.32 (m, 1H), 7.16-7.22 (m, 3H), 4.36 (dd, 1H), 3.18-3.31 (m, 1H), 2.73-2.97 (m, 2H), 1.19 (b, 2H). $^{31}$P NMR (CD$_2$Cl$_2$): δ-5.84 ppm.

Example 4.4

(1R,2R)-2-(Diphenylphosphino)-2,3-dihydro-1H-inden-1-amine

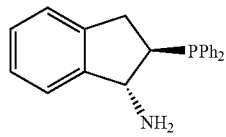

The $^1$H NMR spectrum for this compound was similar to that of (1S,2S)-2-(diphenylphosphino)-2,3-dihydro-1H-inden-1-amine (Example 4.5).

Example 4.5

(S)-2-((Diphenylphosphino)methyl)pyrrolidine

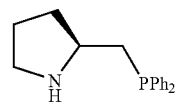

The $^1$H NMR spectra was similar to that reported by Guo et al. J. Am. Chem. Soc. 2005, 127, 516-517.

Example 4.6

(R)-2-((Diphenylphosphino)methyl)pyrrolidine

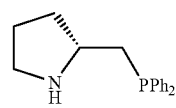

The $^1$H NMR spectra was similar to that reported by Guo et al. J. Am. Chem. Soc. 2005, 127, 516-517.

Example 4.7

(1S,2S)-1-(Diphenylphosphino)-1-phenylpropan-2-amine

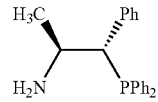

Yield: 93.2%. $^1$H NMR (CD$_2$Cl$_2$) δ 7.53-7.62 (m, 2H), 7.01-7.50 (m, 13H), 2.93-3.02 (m, 1H), 1.65 (b, 2H), 1.00 (d, J=6.6 Hz, 3H). $^{31}$P NMR (CD$_2$Cl$_2$) δ -8.7 ppm.

Example 4.8

(1R,2R)-1-(Diphenylphosphino)-1-phenylpropan-2-amine

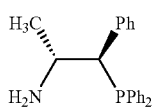

The $^1$H NMR spectrum for this compound was similar to that of (1S,2S)-2-(diphenylphosphino)-1-phenylpropan-1-amine (Example 4.7).

Preparation of Aminophosphephine Ligands

Example 5.1

2-((11bR)-3H-Dinaphtho[2,1-c:1',2'-e]phosphepin-4 (5H)-yl)ethanamine

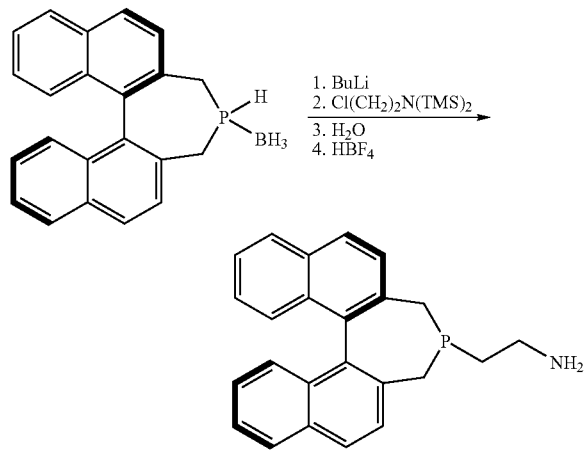

Figure 2:
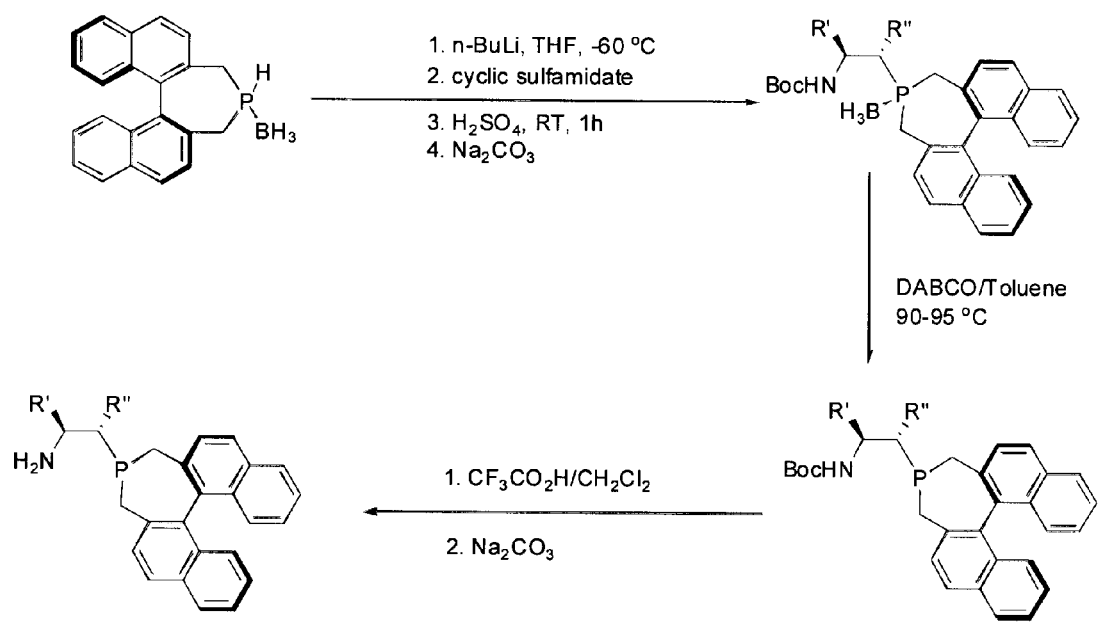
FIG. 2 is a schematic showing the method of producing an aminophosphine ligand in accordance with an embodiment of the disclosure.

Butyl lithium (34 ml of a 2.5 M solution in hexane) was added to a solution of (11bR)-4,5-dihydro-3H-dinaphtho[2,1-c:1',2'-e]phosphepine borane (28.0 g, 86 mmol) in THF (250 ml) at -78° C. The mixture was stirred at -78° C. for 1.5 hour, and a solution of N,N'-bis(trimethylsilyl)-2-chloroethanamine (19.2 g, 86 mmol) in THF (20 ml) added. The reaction mixture was allowed to slowly warm to room temperature and refluxed for 24 hours. The mixture was hydrolyzed with H$_2$SO$_4$ solution, then neutralized with NaOH solution. Workup resulted in crude 2-((11bR)-3H-dinaphtho[2,1-c:1',2'-e]phosphepin-4(5H)-yl)ethanamine borane (36.6 g), which was purified by silica gel chromatography (eluent=EA/CH$_2$Cl$_2$ (1:8, then 1:6)) to give pure 2-((11bR)-3H-dinaphtho[2,1-c:1',2'-e]phosphepin-4(5H)-yl)ethanamine borane (17.5 g). A general procedure for the method of producing aminophosphepine ligands is shown in FIG. 2.

Tetrafluoroboric acid (HBF$_4$.Et$_2$O, 3.4 ml) was added to the solution of 2-((11bR)-3H-dinaphtho[2,1-c:1',2'-e]phosphepin-4(5H)-yl)ethanamine borane (2.0 g) in CH$_2$Cl$_2$ (50 ml) at 0° C. The mixture was stirred at room temperature overnight. Saturated NaHCO$_3$ solution (2×100 ml) was added and the mixture stirred for 1 hour. The aqueous layer was extracted with CH$_2$Cl$_2$ (2×50 ml) and the combined organic layer was washed with 4.0 M NaOH solution (2×100 ml) and brine, then dried (MgSO$_4$). The mixture was filtered and evaporated under reduced pressure to give the crude product as a white foamy solid. Purification by silica gel chromatography (eluent=ethyl acetate (EA)/CH$_2$Cl$_2$ (1:2)) gave the pure product. Yield=1.7 g. $^1$H NMR(C$_6$D$_6$): δ 7.03-7.88 (m, 12H), 2.85 (m, 2H, CH$_2$), 2.05 (m, 2H, CH$_2$), 1.76 (br, 2H, NH$_2$), 1.53 (m, 2H, CH$_2$), 1.35 (m, 2H, CH$_2$). $^{31}$P NMR (C$_6$D$_6$): δ 2.0 (s).

Example 5.2.1

(1S,2S)-1,2-diphenyl-2-(S)-phosphepinoethyleneamine-N-Boc-P-borane complex

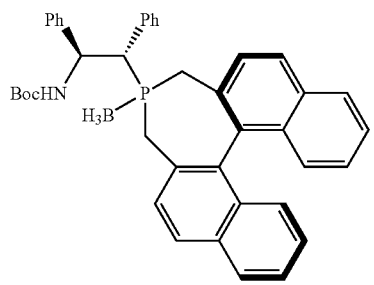

A solution of n-Butyllithium (12 ml, 2.5 M in Hexane) was slowly added to a solution of (11bS)-4,5-dihydro-3H-dinaphtho[2,1-C:1',2'-e]-phosphepine borane complex (9.4 g) in THF (100 ml) in a dry ice/acetone bath. The mixture was stirred for 1 h in the dry ice/acetone bath, then it was added to the suspension of (4S,5R)-4,5-diphenyl-3-alkoxycarbonyl-1,2,3-oxathiazolidine-2-dioxide (10 g) in THF (200 ml) cooled in a dry-ice/acetone bath. The mixture was stirred for 1 h. It was slowly warmed up to the RT and was stirred for 24 h. H$_2$SO$_4$ (20 ml, 2N) was added to the mixture which was stirred at RT for 1 h. Na$_2$CO$_3$ (saturated 50 ml) in brine (20%, 100 ml) was added to neutralize the mixture and make the solution basic. The aqueous layer was extracted with CH$_2$Cl$_2$ (50 ml). The combined organic layer was washed with brine (100 ml×2) and dried over MgSO$_4$ for 2 h. It was filtered and the filtrate was concentrated to almost dryness to give the crude product as a pale yellow solid (17 g) which was dissolved in CH$_2$Cl$_2$ (100 ml). Hexane (400 ml) was added slowly to precipitate the product. The resulting slurry was stirred at RT for 4 h. The solid was filtered and washed with Hexane (50 ml). It was dried under vacuum to give the product as a colorless crystalline solid (12.4 g). Another potion of product obtained from mother liquor (1.6 g). Overall yield is 84.7%. $^1$H NMR (CD$_2$Cl$_2$) δ 7.89-7.94 (m, 2H), 7.79-7.83 (m, 2H), 6.90-7.43 (m, 18H), 6.26 (b, 1H), 5.24 (m, 1H), 3.6

(m, 1H), 2.46-2.56 (m, 1H), 2.38 (b, 1H), 2.04-2.14 (m, 1H). $^{31}$P NMR (CD$_2$Cl$_2$) δ 49.8 ppm.

Example 5.2.2

(1S,2S)-1,2-diphenyl-2-(S)-phosphepineethyleneamine-N-Boc

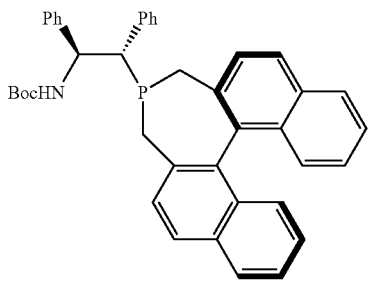

DABCO (3.1 g) was added to the suspension of (1S,2S)-1,2-diphenyl-2-(S)-phosphepine ethyleneamine-N-Boc-P-borane complex (13.5 g) in toluene (150 ml). The mixture was stirred at 90-95° C. under argon overnight. All the volatiles were removed under vacuum. To the residue, CH$_3$CN/MeOH (1:1, 80 ml) was added and the mixture was stirred for. It was filtered and the solid was washed with CH$_3$CN/MeOH (1:1, 30 ml) to give the pure product as a white solid (12 g, yield: 90.9%). $^1$H NMR (CD$_2$Cl$_2$) δ 8.01 (dd, J$_1$=5.1 Hz, J$_2$=8.4 Hz, 2H), 7.87 (dd, J$_1$=8.4 Hz, J$_2$=14.7 Hz, 2H), 7.06-7.46 (m, 16H), 6.83 (b, 2H), 5.48 (b, 1H), 5.34 (b, 1H), 3.12-3.15 (m, 1H), 2.50-2.71 (m, 2H), 1.83-1.95 (m, 2H), 1.47 (s, 9H). $^{31}$P NMR (CD$_2$Cl$_2$) δ 9.08 ppm.

Example 5.2.3

(1S,2S)-1,2-diphenyl-2-(S)-phosphepineethyleneamine

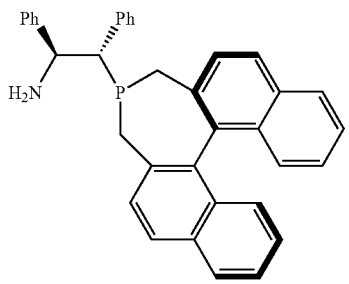

Trifloroacetic acid (30 ml) was added to the solution of (1S,2S)-1,2-diphenyl-2-(S)-phosphepine ethyleneamine-N-Boc (12 g) in CH$_2$Cl$_2$ (100 ml) at 0° C. The mixture was stirred at RT overnight. The volatiles were removed under vacuum and the residue was dissolved in CH$_2$Cl$_2$ (150 ml). It was neutralized with Na$_2$CO$_3$ (saturated, 50 ml) in brine (20%, 100 ml). The aqueous layer was extracted with CH$_2$Cl$_2$ (100 ml). The combined organic layer was washed with brine (20%) and dried over MgSO$_4$ for 3 h. The solvent was removed to give the crude product as a white solid (9 g) which was purified by dissolving in CH$_3$CN/MeOH (1:1, 80 ml), then water (100 ml) was added slowly to precipitate the product. It was filtered and dried to give the pure product as a white solid (7.2 g, yield: 72%). $^1$H NMR (CD$_2$Cl$_2$) δ 8.05 (dd, J$_1$=8.3 Hz, J$_2$=22.2 Hz, 2H), 7.88 (dd, J$_1$=7.2 Hz, J$_2$=15.5 HZ, 2H), 7.63 (d, J=7.2 Hz, 1H), 6.73-7.47 (m, 17H), 4.47 (dd, J$_1$=5.1 Hz, J$_2$=9.2 Hz, 1H), 3.31 (dd, J$_1$=5.0 Hz, J$_2$=14.0 Hz, 1H), 3.06 (dd, J$_1$=6.6 Hz, J$_2$=9.3 Hz, 1H), 2.61 (dd, J$_1$=11.4 Hz, J$_2$=14.3 Hz, 1H), 1.89 (m, 4H). $^{31}$P NMR (CD$_2$Cl$_2$) δ 14.9 ppm.

Example 5.3.1

(1S,2S)-1-methyl-2-diphenyl-2-(S)-phosphepinoethyleneamine-N-Boc-P-borane complex

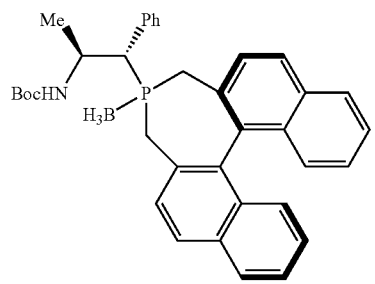

A solution of n-Butyllithium (17 ml, 2.5 M in Hexane) was slowly added to a solution of (11bS)-4,5-dihydro-3H-dinaphtho[2,1-C:1',2'-e]-phosphepine borane complex (13.8 g) in THF (100 ml) cooled in a dry ice/acetone bath. The mixture was stirred for 1 h with cooling in a dry ice/acetone bath, then it was added to a suspension of (4S, 5R)-4-methyl-5-phenyl-3-alkoxycarbonyl-1,2,3-oxathiazolidine-2,2-dioxide (12.1 g) in THF (100 ml) cooled in a dry-ice/acetone bath. The mixture was stirred for 1 h. It was slowly warmed up to the RT and was stirred for 24 h. H$_2$SO$_4$ (20 ml, 2N) was added to the mixture which was stirred at RT for 1 h. Na$_2$CO$_3$ (saturated 50 ml) in brine (20%, 100 ml) was added to neutralize the mixture and make the solution basic. The aqueous layer was extracted with CH$_2$Cl$_2$ (50 ml). The combined organic layer was washed with brine (100 ml×2) and dried over MgSO$_4$ for 2 h. It was filtered and the filtrate was concentrated to almost dryness to give the crude product as a white solid (20 g) which was dissolved in CH$_2$Cl$_2$ (80 ml), hexane (400 ml) was added slowly to precipitate the product. The resulting slurry was stirred at RT for 4 h. The solid was filtered and washed with Hexane (50 ml). It was dried under vacuum to give the product as a colorless crystalline solid (15.5 g, yield: 71.8%). $^1$H NMR (CD$_2$Cl$_2$) δ 7.83-7.97 (m, 6H), 7.30-7.40 (m, 4H), 6.96-7.16 (m, 7H), 4.90 (b, 1H), 4.08 (m, 1H), 3.46 (m, 1H), 3.12 (dd, J=5.0 Hz, J=14.6 Hz, 1H), 2.67 (dd, J=6.4 Hz, J=14.6 Hz, 1H), 1.90-2.34 (m, 2H). $^{31}$P NMR (CD$_2$Cl$_2$) δ 50.2 ppm.

Example 5.3.2

(1S,2S)-1-methyl-2-diphenyl-2-(S)-phosphepinoethyleneamine-N-Boc

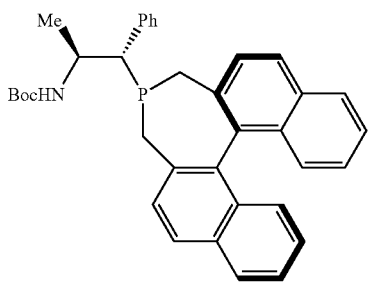

DABCO (6.4 g) was added to a suspension of (1S,2S)-1-methyl-2-diphenyl-2-(S)-phosphepinoethyleneamine-N-Boc-Phosphepine-borane complex (15.5 g) in toluene (250 ml). The mixture was stirred at 90-95° C. under argon overnight. All the volatiles were removed under vacuum. To the residue, $CH_3CN/MeOH$ (1:1, 80 ml) was added and the mixture was stirred for 6 h to remove impurities. It was filtered and the solid was washed with $CH_3CN/MeOH$ (1:1, 30 ml) to give the pure product as a white solid (10.7 g, yield: 70.1%). $^1H$ NMR ($CD_2Cl_2$) δ 7.74-7.91 (m, 5H), 6.95-7.35 (m, 12H), 4.15-4.38 (m, 2H), 2.78-2.85 (m, 2H), 2.50 (dd, J=10.6 Hz, J=14.4 Hz, 1H), 1.96 (dd, J=11.8 Hz, J=14.9 Hz, 1H), 1.75 (dd, J=3.1 Hz, 11.9 Hz, 1H), 1.43 (s, 9H), (m, 2H), 1.11 (d, J=6.7 Hz, 3H). $^{31}P$ NMR ($CD_2Cl_2$) δ 10.6 ppm.

Example 5.3.3

(1S,2S)-1-methyl-2-diphenyl-2-(S)-phosphepinoethylamine

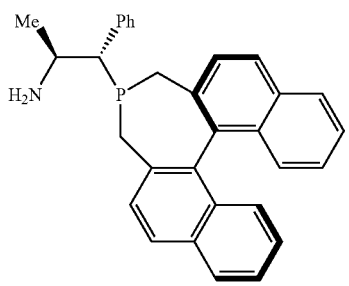

Trifluoroacetic acid (30 ml) was added to a solution of (1S,2S)-1-methyl-2-diphenyl-2-(S)-phosphepinoethylamine-N-Boc (10.7 g) in $CH_2Cl_2$ (100 ml) at 0° C. The mixture was stirred at RT overnight. The volatiles were removed under vacuum and the residue was dissolved in $CH_2Cl_2$ (200 ml). It was neutralized with $Na_2CO_3$ (saturated, 50 ml) in brine (20%, 100 ml). The aqueous layer was extracted with $CH_2Cl_2$ (100 ml). The combined organic layer was washed with brine (20%) and dried over $MgSO_4$ for 3 h. The solvent was removed to give the crude product as a white solid (8.3 g) which was purified by filtering through a silica gel pad (eluent: $CH_2Cl_2$/hexane, 1/1, 300 ml to remove impurities, $CH_2Cl_2$/THF, 9/1, 200 ml to elute the product). The solvent was removed from the filtrate to give the product as a colorless solid (7.2 g, yield: 82.4%). $^1H$ NMR ($CD_2Cl_2$) δ 7.83-8.04 (m, 4H), 6.94-7.58 (m, 13H), 3.43-3.53 (m, 1H), 3.16 (dd, J=5.2 Hz, J=14.2 Hz, 1H), 2.53-2.62 (m, 2H), 1.86-1.90 (m, 2H), 1.29 (b, 2H), 1.07 (d, J=6.3 Hz, 3H), 1.89 (m, 4H). $^{31}P$ NMR ($CD_2Cl_2$) δ 14.6 ppm.

Example 5.4.1 tert-Butyl-2-((11bS)-3H-dinaphtho[2,1-c:1',2'-e]phosphepin-4(5H)-yl)ethylcarbamate-P-borane complex

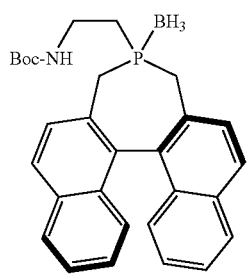

A solution of n-Butyllithium (2.1 ml, 2.5 M in Hexane) was added to the solution of (11bS)-4,5-dihydro-3H-dinaphtho[2,1-C:1',2'-e]-phosphepine borane complex (1.6 g) in THF (30 ml) with a dry ice/acetone bath at −50° C. The mixture was stirred for 20 minutes at −50° C. and was then added to a solution of 3-alkoxycarbonyl-1,2,3-oxathiazolidine-2,2-dioxide (1.0 g) in THF (20 ml). The mixture was slowly warmed to RT and was stirred overnight. A solution of $H_2SO_4$ (5 ml, 2N) followed by brine (10 ml) were added and the resulting solution was stirred at RT for 20 minutes. A solution of $Na_2CO_3$ (saturated, 10 ml) was added to neutralize the mixture. The aqueous layer was extracted using $CH_2Cl_2$ (50 ml) and the combined organic layer was washed with brine (100 ml×2) and dried over $MgSO_4$ for 2 hours. The solution was filtered and concentrated under vacuum to generate the crude residue. This was dissolved in $CH_2Cl_2$ (50 ml) and filtered using a silica gel pad with $CH_2Cl_2$ as the eluent (200 ml). The solvent was removed under vacuum to give the pure product (2.0 g, yield: 90%). $^1H$ NMR ($CD_2Cl_2$) δ 5.0 (b, 1H), 7.1-8.0 (m, 16H) $^{31}P$ NMR ($CD_2Cl_2$) δ 44.9 ppm (b).

Example 5.4.2 tert-Butyl-2-((11bS)-3H-dinaphtho[2,1-c:1',2'-e]phosphepin-4(5H)-yl)ethylcarbamate

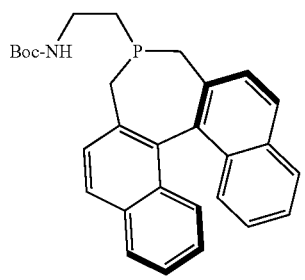

DABCO (0.62 g) was added to a solution of tert-butyl-2-((11bS)-3H-dinaphtho[2,1-c:1',2'-e]phosphepin-4(5H)-yl)

ethylcarbamate-P-borane complex (2.0 g) in toluene (50 ml). The solution mixture was stirred at 90° C. overnight. The solvent was removed under vacuum to give a solid crude product which was then dissolved in CH$_3$CN/MeOH 1:1 (30 ml). Water (20 ml) was added and the solvent was decanted. The remaining residue was dried under vacuum to give the product as a white solid (1.6 g, yield: 82.4%). $^{31}$P NMR (CD$_2$Cl$_2$) δ −0.1 ppm.

Example 5.4.3

2-((11bS)-3H-dinaphtho[2,1-c:1',2'-e]phosphepin-4 (5H)-yl)ethanamine

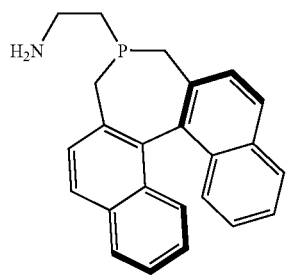

Trifluoroacetic acid (3.5 ml) was added to a solution of tert-butyl-2-((11bS)-3H-dinaphtho[2,1-c:1',2'-e]phosphepin-4(5H)-yl)ethylcarbamate (1.6 g) in CH$_2$Cl$_2$ (30 ml) at room temperature. The mixture was stirred at RT overnight following which all volatiles were removed. The residue was dissolved in CH$_2$Cl$_2$ (50 ml) and the solution was neutralized with Na$_2$CO$_3$ (saturated, 50 ml) in brine (20%, 50 ml). The aqueous layer was then extracted with CH$_2$Cl$_2$ (60 ml) and the combined organic layer was washed with brine (20%, 150 ml) and dried over MgSO$_4$ for 2 hours. The organic solution was filtered and concentrated under vacuum to give a crude white product (1.1 g, yield: 88%). The product was washed with hexane (100 ml) to give a pure white solid product (0.8 g, yield: 64.3%). $^{31}$P NMR (CD$_2$Cl$_2$) δ 0.6, −1.4 ppm.

Example 6

N-((1S,2S)-2-((4R,11bS)-3H-dinaphtho[2,1-c:1',2'-e] phosphepin-4{5H)-yl)-1,2-diphenylethyl)-1,2-diphenylphosphinamine

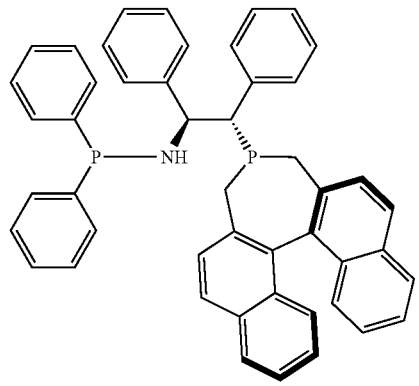

Chlorodiphenyl phosphine (121 mg) was added to a solution of (1S,2S)-1,2-diphenyl-2-(S)-phosphepine ethyleneamine (254 mg) in triethylamine (101 mg), DMAP (5 mg) and CH$_2$Cl$_2$ (30 ml) at room temperature. The mixture was stirred at RT overnight. The solvent was removed and the residue was filtered using a silica gel pad with CH$_2$Cl$_2$ as the eluent (60 ml). The filtered solution was concentrated and dried under vacuum to give the colourless solid product (185 mg, yield: 53.5%). $^{31}$P NMR (CD$_2$Cl$_2$) δ 42.52 (d, J=5.1 ppm); 12.02 (d, J=5.1 ppm).

Example 7

N-((1S,2S)-2-((4R,11bS)-3H-dinaphtho[2,1-c:1',2'-e] phosphepin-4(5H)-yl)-1,2-diphenylethyl)-1,1-bis(3, 5-(trifluoromethylphenyl)phosphinamine

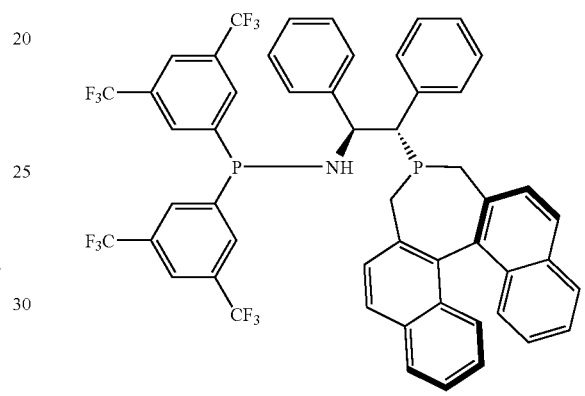

Chlorodi(3,5-trifluoromethylphenyl) phosphine (270 mg) was added to the solution of (1S,2S)-1,2-diphenyl-2-(S)-phosphepine ethyleneamine (254 mg) in triethylamine (101 mg), DMAP (5 mg) and CH$_2$Cl$_2$ (30 ml) at room temperature. The mixture was stirred at RT for four hours. The solvent was removed under vacuum and the crude product was purified using a silica gel pad with CH$_2$Cl$_2$ as the eluent (60 ml). The filtered solution was dried under vacuum to give the product as a pale-yellow solid (335 mg, yield: 69.6%). $^{31}$P NMR Example 8

(11bS)-N-((1S,2S)-2-((4R,11bS)-3H-dinaphtho[2,1-c:1',2'-e]phosphepin-4(5H)-yl)-1,2-diphenylethyl) dinaphtho[2,1-d:1',2'-f][1,3,2]dioxaphosphepin-4-amine

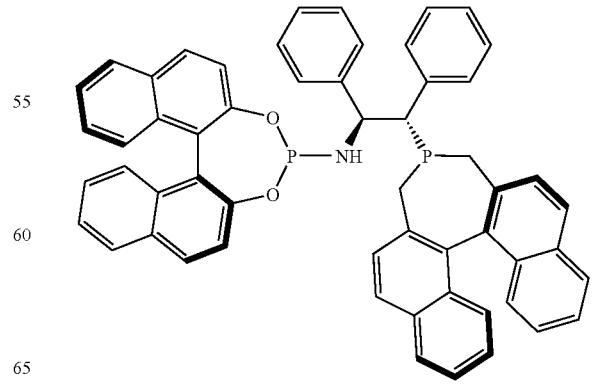

A portion of (11bR)-4-chlorodinaphtho[2,1-d:1',2'-f][1,3,2]dioxaphosphepine (210 mg) was added to the solution of (1S,2S)-1,2-diphenyl-2-(S)-phosphepineethyleneamine (254 mg) in triethylamine (101 mg), DMAP (5 mg) and CH$_2$Cl$_2$ (30 ml) at room temperature. The mixture was stirred at RT for three hours. The solvent was removed under vacuum and the crude product was filtered using a silica gel pad with CH$_2$Cl$_2$ as the eluent (60 ml). The filtered solution was dried under vacuum to give the product as a white solid product (260 mg, yield: 64%). $^{31}$P NMR (CD$_2$Cl$_2$) δ 152.4 (d, J=26.7 Hz); 14.4 (d, J=26.7 Hz).

Example 9

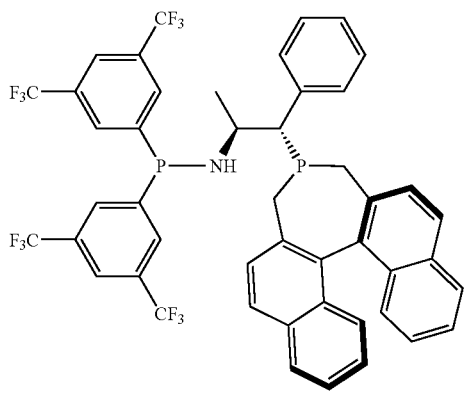

Chlorodi(3,5-trifluoromethylphenyl) phosphine (270 mg) was added to a solution of (1S,2S)-1-methyl-2-diphenyl-2-(S)-phosphepinoethylamine (223 mg) in triethylamine (101 mg), DMAP (5 mg) and CH$_2$Cl$_2$ (30 ml) at room temperature. The mixture was stirred at RT for four hours. The solvent was removed under vacuum and the crude product was purified using a silica gel pad with CH$_2$Cl$_2$ as the eluent (60 ml). The filtered solution was dried under vacuum to give the product as a pale-yellow solid (320 mg, yield: 71%). $^{31}$P NMR (CD$_2$Cl$_2$) δ 39.10 (d, J=1.9 Hz); 10.83 (d, J=1.9 Hz).

Example 10

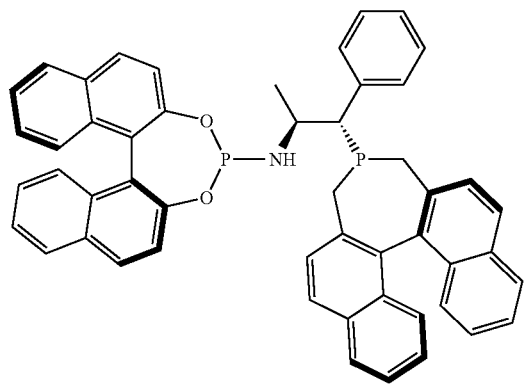

A portion of (11bS)-4-chlorodinaphtho[2,1-d:1',2'-f][1,3,2]dioxaphosphepine (210 mg) was added to a solution of (1S,2S)-1-methyl-2-diphenyl-2-(S)-phosphepinoethylamine (223 mg) in triethylamine (101 mg), DMAP (5 mg) and CH$_2$Cl$_2$ (30 ml) at room temperature. The mixture was stirred at RT for three hours. The solvent was removed under vacuum and the crude product was filtered using a silica gel pad with CH$_2$Cl$_2$ as the eluent (60 ml). The filtered solution was dried under vacuum to give the product as a white solid (230 mg, yield: 61.6%). $^{31}$P NMR (CD$_2$Cl$_2$) δ 152.88 (d, J=25.5 Hz); 13.87 (d, J=25.5 Hz).

Preparation of Aminophosphine Ligands from Ephedrine

Example 11.1

(4S,5R)-3,4-dimethyl-5-phenyl-1,2,3-oxathiazolidine-2-oxide

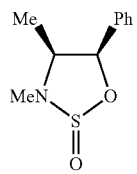

Figure 3:
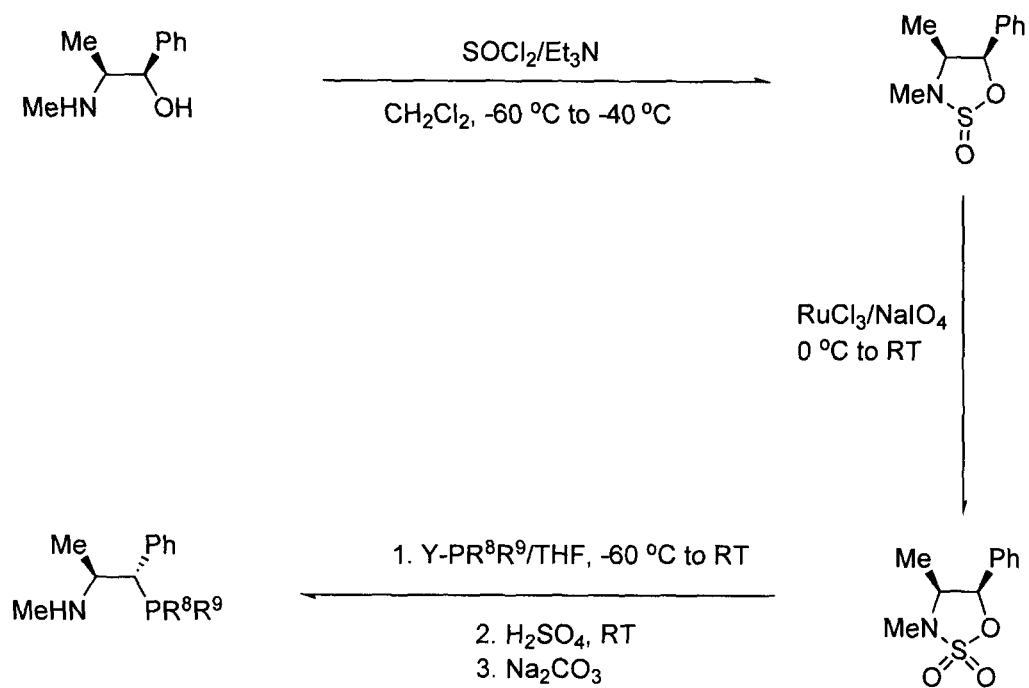
FIG. 3 is a schematic showing the method of producing an aminophosphine ligand in accordance with an embodiment of the disclosure.

A solution of SOCl$_2$ (7.2 g) in CH$_2$Cl$_2$ (50 ml) was added to a solution of (1R,2S)-ephedrine (8.3 g) and triethylamine (20 g) in CH$_2$Cl$_2$ (300 ml) at −40° C. The mixture was stirred at −40° C. for 2 h. Water (50 ml) was added to quench the reaction. The mixture was allowed to warm up to RT, then water (500 ml) was added. The aqueous layer was extracted with CH$_2$Cl$_2$ (100 ml×2). The combined organic layer was washed with brine (20%, 800 ml) and was dried over MgSO$_4$. It was filtered with a silica gel pad (eluent: CH$_2$Cl$_2$/ethyl acetate=1:1). The solvent was removed to give the crude cyclic sulfamidite as a brown oil which solidified upon standing (6.4 g). The product was sufficiently pure for the next step. A general procedure for the method of producing aminophosphine ligands from ephedrine is shown in FIG. 3.

Example 11.2

(4S,5R)-3,4-dimethyl-5-phenyl-1,2,3-oxathiazolidine-2,2-dioxide

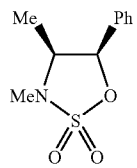 [SMILES: C[C@H]1[C@@H](c2ccccc2)OS(=O)(=O)N1C]

A weighed amount of RuCl$_3$.nH$_2$O (20 mg) was added to a mixture of (4S,5R)-3,4-dimethyl-5-phenyl-1,2,3-oxathiazolidine-2-oxide (6.4 g) in CH$_3$CN (150 ml), CH$_2$Cl$_2$ (20 ml) and H$_2$O (150 ml). This was followed by the addition of NaIO$_4$ (8 g) at 0° C. The color of mixture changed to yellow. It was stirred at 0° C. for 1 h, then RT for 1 h. The aqueous layer was extracted with ether (100 ml×2). The combined organic layer was washed with brine (200 ml×3) and dried over MgSO$_4$. The filtrate was concentrated to almost dryness. The residue was crystallized from ethyl acetate (15 ml) and Hexane (300 ml). The crystalline solid was filtered and dried to give the product (6 g, yield: 52% two steps). $^1$H NMR (CD$_2$Cl$_2$) δ 7.38-7.45 (m, 5H), 5.71 (d, J=6.75 Hz, 1H), 3.88-3.93 (m, 1H), 2.76 (s, 3H), 0.87 (d, J=6.6 Hz, 3H).

Example 11.3

(1S,2S)-1-methyl-2-phenyl-2-diphenylphosphino-N-methylethyleneamine

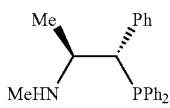

A solution of KPPh$_2$ (54 ml, 0.5 M in THF) was added dropwise to a suspension of (4S,5R)-3,4-dimethyl-5-phenyl-1,2,3-oxathiazolidine-2,2-dioxide (5.9 g) in THF (150 ml) cooled in an acetone/dry-ice bath. The mixture was stirred at −60° C. for 0.5 h. It was slowly warmed up to the RT and stirred overnight. A solution of H$_2$SO$_4$ (10 ml, 2N) in brine (20%, 100 ml) was added to the mixture and it was stirred at RT for 1 h. Na$_2$CO$_3$ (saturated 50 ml) was added to neutralize the mixture and make the solution basic. The aqueous layer was extracted with CH$_2$Cl$_2$ (50 ml×2). The combined organic layer was washed with brine (150 ml×2) and dried over MgSO$_4$ for 2 h. It was filtered and the filtrate was concentrated to almost dryness. The residue was purified with a silica gel pad (eluent: CH$_2$Cl$_2$/Hexane 1/1 to remove the impurities, then CH2Cl2/THF 19/1 to washed out the product. The solvent was removed to give the product as a colorless solid (7.3 g, yield: 84%). $^1$H NMR (CD$_2$Cl$_2$) δ 7.60-7.70 (m, 2H), 7.06-7.39 (m, 13H), 3.91 (dd, J=4.4 Hz, J=6.4 Hz, 1H), 2.63-2.68 (m, 1H), 2.33 (s, 3H), 1.11 (d, J=6.6 Hz, 3H). $^{31}$P NMR (CD$_2$Cl$_2$) δ −9.9.

Example 12

(11bS)-N-((1S,2S)-2-(diphenylphosphino)-1,2-diphenylethyl)dinaphtho[2,1-d:1',2'-f][1,3,2]dioxaphosphepin-4-amine

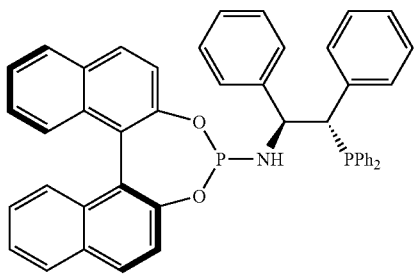

A portion of (11bR)-4-chlorodinaphtho[2,1-d:1',2'-f][1,3,2]dioxaphosphepine (210 mg) was added to a solution of (1S,2S)-1,2-diphenyl-2-diphenylphosphinoethyleneamine (190 mg) in triethylamine (101 mg), DMAP (5 mg) and CH$_2$Cl$_2$ (30 ml) at room temperature. The mixture was stirred at RT for three hours. The solvent was removed under vacuum and the crude product residue was filtered using a silica gel pad with CH$_2$Cl$_2$ as the eluent (60 ml). The remaining eluent in the filtered solution was evaporated under vacuum to give the white solid product (251 mg, yield: 72.1%). $^{31}$P NMR (CD$_2$Cl$_2$) δ 153.4 (d, J=12.1 Hz); 13.87 (d, J=12.1 Hz).

Example 13

General Procedure for Preparation of New Aminophosphine Catalysts

The new catalysts (S-Binap)((1S,2S)-2-(diphenylphosphino)-1,2-diphenylethanamine) and (S-Binap)((1S,2S)-2-(Diphenylphosphino)-2,3-dihydro-1H-inden-1-amine) were prepared using the general procedure below.

Tetrahydrofuran (20 ml) was added to a mixture of the S-binap ligand (0.5 g, 0.8 mmol) and [RuCl$_2$(benzene)]$_2$ (200 mg, 0.4 mmol), followed by DMF (0.5 ml) and the mixture refluxed for 6 hours under argon. The solvent was removed under reduced pressure and a solution of the aminophosphine (0.8 mmol) in toluene 20 added. The mixture was refluxed for 4 hours and the solvent removed under reduced pressure. Ether (10 ml) was then added and the mixture stirred for 2 hours under argon. The solids were filtered, washed with ether and dried under vacuum. The catalysts were used for the hydrogenation of acetophenone without further purification.

Example 14

Catalytic Hydrogenation of Acetophenone Using New Catalysts

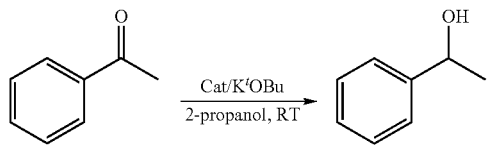

A solution of acetophenone (1.0 g, 8.3 mmol) in 2-propanol (10 ml) was added to a 50 mL Schlenk flask. After degassing and refilling with argon, a mixture of the catalyst (0.01 mmol) and K$^t$OBu (0.18 mmol) were added. The resulting mixture was then injected into a 100 mL autoclave under an atmosphere of H$_2$ gas. The autoclave was pressurized to 200 psig and the reaction mixture was stirred at ambient temperature. Upon completion of the reaction, the solvent was removed under vacuum and the mixture was filtered through a silica gel pad (ca. 6 cm) using 3:1 hexane:ethyl acetate. The solvent was removed from the filtrate affording the product as a colorless liquid. Results are shown in Table 1.

Example 15

General Procedure for Enamide Hydrogenation

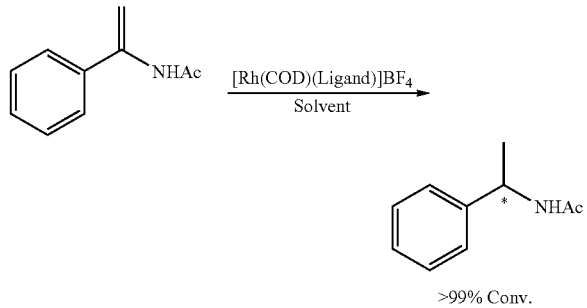

-continued

L1

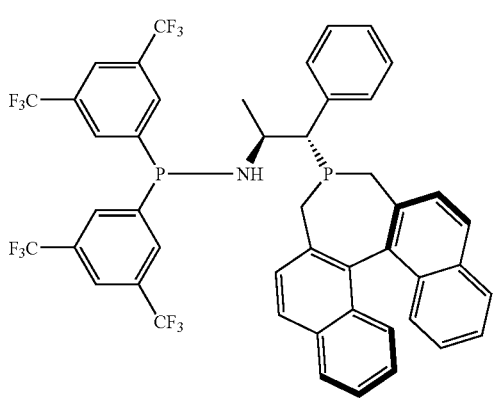

L2

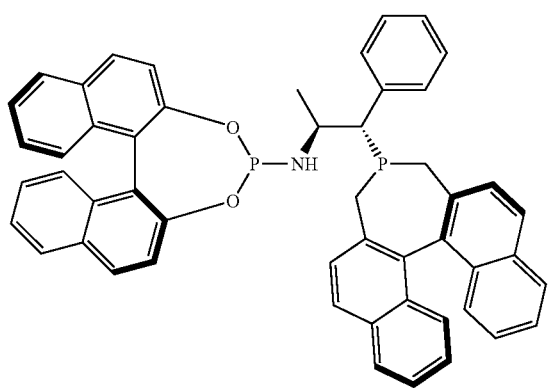

A solution of the substrate (1 mmol) was injected into an autoclave and the desired solvent (7 ml) was added. The resulting mixture was degassed with hydrogen several times. The rhodium catalyst (0.002 mmol) in the corresponding solvent (1 ml) was added. The mixture was pressured with hydrogen (100 psi) and stirred at ambient temperature for 10 h. The conversion and enantiomeric excess was determined with GC. The results are shown in Table 2.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

FULL CITATIONS FOR DOCUMENTS REFERRED TO IN THE SPECIFICATION (1) (a) Mikami, K.; Korenaga, T.; Terada, M.; Ohkuma, T.; Pham, T.; Noyori, R. *Angew. Chem., Int. Ed.* 1999, 38, 495-497. (b) Doucet, H.; Ohkuma, T.; Murata, K.; Yokozawa, T.; Kozawa, M.; Katayama, E.; England, A. F.; Ikariya, T.; Noyori, R. *Angew. Chem., Int. Ed.* 1998, 37, 1703-1707. (c) Ohkuma, T.; Ooka, H.; Ikariya, T.; Noyori, R. *J. Am. Chem. Soc.* 1995, 117, 10417-10418.

(2) (a) Ohkuma, T.; Koizumi, M.; Doucet, H.; Pham, T.; Kozawa, M.; Murata, K.; Katayama, E.; Yokozawa, T.; Ikariya, T.; Noyori, R. *J. Am. Chem. Soc.* 1998, 120, 13529-13530. (b) Ohkuma, T.; Doucet, H.; Pham, T.; Mikami, K.; Korenaga, T.; Terada, M.; Noyori, R. *J. Am. Chem. Soc.* 1998, 120, 1086-1087. (c) Ohkuma, T.; Ooka, H.; Yamakawa, M.; Ikariya, T.; Noyori, R. *J. Org. Chem.* 1996, 61, 4872-4873.

(3) (a) Abdur-Rashid, K.; Lough, A. J.; Morris, R. H. *Organometallics* 2001, 20, 1047-1049. (b) Abdur-Rashid. K; Lough, A. J.; Morris, R. H. *Organometallics* 2000, 19, 2655-2657.

(4) (a) PCT Int. Appl. WO 02/22526 A2. (b) Abdur-Rashid, K.; Guo, R.; Lough, A. J.; Morris, R. H. *Adv. Synth. Catal.* 2005, 347, 571-579. (c) Guo, R.; Lough, A. J.; Morris, R. H.; Song, D. *Organometallics* 2004, 23, 5524-5529. (d) Guo, R.; Lough, A. J.; Morris, A. J.; Song, D. *Organometallics* 2005, 24 3354-3354.

TABLE 1

Results of Hydrogenation of Acetophenone

| Entry | Catalyst | Time (h) | Conv. (%) | e.e. (%) |
| --- | --- | --- | --- | --- |
| 1 | | 3 | >99 | 69 |

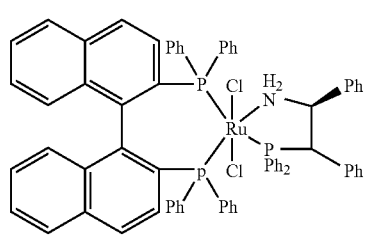

R-Binap, S,S-Aminophosphine

TABLE 1-continued

Results of Hydrogenation of Acetophenone

| Entry | Catalyst | Time (h) | Conv. (%) | e.e. (%) |
|---|---|---|---|---|
| 2 | S-Binap, S,S-Aminophosphine | 3 | >99 | 26 |
| 3 | S,S,S-Aminophosphine | 6 | 80 | 32 |
| 4 | S,S-Aminophosphine | 0.5 | >99 | 36 |
| 5 | R-Binap, S,S-Aminophosphine | 7 | 95 | 24 |

TABLE 2

Results for Enamide Hydrogenation

| Ligand | Solvent | Conv. % | e.e. % |
|---|---|---|---|
| L1 | MeOH | >99 | 55 |
| L1 | Acetone | >99 | 40 |
| L1 | $CH_2Cl_2$ | >99 | 66 |
| L2 | MeOH | >99 | 45 |
| L2 | Acetone | >99 | 58 |
| L2 | $CH_2Cl_2$ | >99 | 74 |

We claim:

1. A method for preparing aminophosphine ligands comprising reacting a compound of the formula I

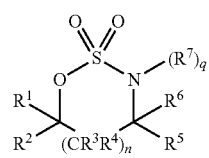

with a metal phosphide reagent of the formula $Y-PR^8R^9$ under conditions to provide, optionally after removal of a protecting group (PG), a compound of the formula II,

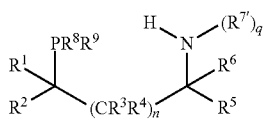

wherein q is 0 or 1;

where when q is 0, the N atom is further linked to any one of $R^1$, $R^2$, $R^3$, $R^4$, $R^5$ or $R^6$;

n is 0, 1, 2, 3 or 4;

Y is a cation;

$R^1$ to $R^6$ are simultaneously or independently selected from H, $C_{2\text{-}20}$alkenyl, $C_{2\text{-}20}$alkynyl, $C_{3\text{-}20}$cycloalkyl, aryl and heteroaryl, said latter 6 groups being optionally substituted, or two adjacent or geminal groups, including the nitrogen atom of the amino group, are linked together to form an optionally substituted monocyclic or polycyclic, metalated, saturated, unsaturated and/or aromatic ring system having 3 or more atoms;

$R^7$ is selected from H, $C_{1\text{-}6}$alkyl, aryl, and a suitable amine protecting group, said alkyl and aryl groups being optionally substituted;

$R^{7'}$ is selected from H, $C_{1\text{-}6}$alkyl, and aryl, said alkyl and aryl groups being optionally substituted;

$R^8$ and $R^9$ are simultaneously or independently selected from H, $C_{1\text{-}20}$alkyl, $C_{2\text{-}20}$alkenyl, $C_{2\text{-}20}$alkynyl, aryl, heteroaryl, $OR^{10}$ and $N(R^{10})_2$, said latter 7 groups being optionally substituted, or $R^8$ and $R^9$ are linked together to form an optionally substituted monocyclic or polycylic, saturated, unsaturated and/or aromatic ring system having 4 or more atoms, including the phosphorous atom to which said $R^8$ and $R^9$ groups are linked, and in which one or more carbon atoms in said monocyclic or polycyclic ring system are optionally replaced with a heteromoiety selected from O, S, N, NH and $NC_{1\text{-}6}$alkyl;

$R^{10}$ is selected from $C_{1\text{-}6}$alkyl, $C_{2\text{-}6}$alkenyl, $C_{2\text{-}6}$alkynyl and aryl, said latter 4 groups being optionally fluoro-substituted;

the optional substituents are selected from one or more of halo, OH, $NH_2$, $OR^{11}$, $N(R^{11})_2$ and $R^{11}$, and $R^{11}$ is selected elected from $C_{1\text{-}6}$alkyl, $C_{2\text{-}6}$alkenyl, $C_{2\text{-}6}$alkynyl and aryl, said latter 4 groups being optionally fluoro-substituted.

2. The method according to claim 1, wherein $R^1$ to $R^6$ are simultaneously or independently selected from the group consisting of H, $C_{1\text{-}10}$alkyl, $C_{2\text{-}10}$alkenyl, $C_{2\text{-}10}$alkynyl, $C_{3\text{-}10}$cycloalkyl, aryl and heteroaryl, said latter 6 groups being optionally substituted, or two adjacent or geminal groups, including the nitrogen atom of the amino group, are linked together to form an optionally substituted monocyclic or polycyclic, metallated, saturated, unsaturated and/or aromatic ring system having 5 or more atoms.

3. The method according to claim 1, wherein $R^7$ is $C_{1\text{-}4}$alkyl or phenyl, said latter two groups being optionally substituted.

4. The method according to claim 1, wherein $R^8$ and $R^9$ are simultaneously or independently selected from H, $C_{1\text{-}10}$alkyl, $C_{2\text{-}10}$alkenyl, $C_{2\text{-}10}$alkynyl and aryl, said latter 4 groups being optionally substituted, or $R^8$ and $R^9$ are linked together to form an optionally substituted monocyclic or polycyclic ring system having 4 or more atoms, including the phosphorous atom to which $R^8$ and $R^9$ are linked, in which the rings are saturated, unsaturated and/or aromatic and in which one or more carbon atoms in said monocyclic or polycyclic ring system are optionally replaced with a heteromoiety selected from O, N, NH and $NC_{1\text{-}6}$alkyl.

5. The method according to claim 1, wherein $R^8$ and $R^9$ are linked to form an optionally substituted fused pentacyclic ring system having 23 atoms, including the phosphorous atom to which $R^8$ and $R^9$ are linked.

6. The method according to claim 5, wherein the fused pentacyclic ring system comprises

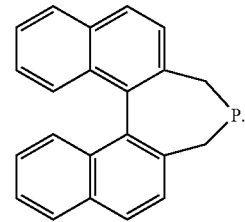

7. The method according to claim 1, wherein PG comprises trimethylsilyl (TMS), acetyl, tert-butyldimethylsilyl (TBDMS), tert-butoxycarbonyl (BOC), benzyloxycarbonyl or 9-fluorenylmethyloxycarbonyl (FMOC).

8. The method according to claim 7, wherein PG comprises trimethylsilyl (TMS).

* * * * *